United States Patent
Kim et al.

(10) Patent No.: US 10,639,009 B2
(45) Date of Patent: May 5, 2020

(54) APPARATUS AND METHOD FOR COMBINED PHOTOACOUSTIC AND ULTRASOUND DIAGNOSIS

(71) Applicants: SAMSUNG MEDISON CO., LTD., Gangwon-Do (KR); The State University of New York Buffalo, Buffalo, NY (US)

(72) Inventors: Jung-Ho Kim, Gangwon-do (KR); Jung-Taek Oh, Seoul (KR); Jonathan Lovell, Buffalo, NY (US); Wentao Song, Buffalo, NY (US); Dal-Kwon Koh, Gangwon-do (KR); Chul-Hong Kim, Buffalo, NY (US); Man-Sik Jeon, Buffalo, NY (US); Jong-Kyu Jung, Gangwon-Do (KR)

(73) Assignees: Samsung Medison Co., Ltd., Hongcheon-gun, Ganwon-do (KR); The State University of New York Buffalo, Buffalo, NY (US)

( * ) Notice: Subject to any disclaimer, the term of this patent is extended or adjusted under 35 U.S.C. 154(b) by 1096 days.

(21) Appl. No.: 14/337,204

(22) Filed: Jul. 21, 2014

(65) Prior Publication Data
US 2015/0025373 A1    Jan. 22, 2015

(30) Foreign Application Priority Data
Jul. 21, 2013    (KR) .......................... 10-2013-0085759

(51) Int. Cl.
*A61B 8/00* (2006.01)
*A61B 5/00* (2006.01)
(Continued)

(52) U.S. Cl.
CPC .......... *A61B 8/4416* (2013.01); *A61B 5/0035* (2013.01); *A61B 5/0095* (2013.01);
(Continued)

(58) Field of Classification Search
None
See application file for complete search history.

(56) References Cited

U.S. PATENT DOCUMENTS

| 2007/0092447 A1 | 4/2007 | Padilla De Jesus et al. |
| 2008/0008658 A1* | 1/2008 | De Haen ............... A61K 31/22 424/9.52 |

(Continued)

FOREIGN PATENT DOCUMENTS

| JP | 2010-037257 A | 2/2010 |
| JP | 2010-520871 A | 6/2010 |

(Continued)

OTHER PUBLICATIONS

Tsutsui et al. ("the sue of microbubbles to target drug delivery", cardiovascular ultrasound, 2004, 2:23).*
(Continued)

*Primary Examiner* — Carolyn A Pehlke
*Assistant Examiner* — Marjan Saboktakin
(74) *Attorney, Agent, or Firm* — Morgan, Lewis & Bockius LLP

(57) ABSTRACT

A microbubble used as a contrast agent for ultrasound imaging burst due to high intensity of ultrasound, and the burst microbubble effectively acts as a contrast agent for photoacoustic imaging. Based on this point, a new apparatus and method for combined photoacoustic and ultrasound diagnosis are provided.

18 Claims, 20 Drawing Sheets

(51) Int. Cl.
   A61B 8/08   (2006.01)
   A61K 49/22  (2006.01)
   A61K 49/00  (2006.01)
   A61M 37/00  (2006.01)
   A61M 31/00  (2006.01)
(52) U.S. Cl.
   CPC ............ *A61B 5/4839* (2013.01); *A61B 8/463* (2013.01); *A61B 8/481* (2013.01); *A61B 8/5246* (2013.01); *A61B 8/5261* (2013.01); *A61K 49/0091* (2013.01); *A61K 49/223* (2013.01); *A61M 31/005* (2013.01); *A61M 37/0092* (2013.01)

(56) References Cited

U.S. PATENT DOCUMENTS

| | | |
|---|---|---|
| 2008/0045865 A1 | 2/2008 | Kislev |
| 2010/0106078 A1 | 4/2010 | Dimitrova et al. |
| 2012/0027679 A1 | 2/2012 | Yamauchi et al. |
| 2012/0203103 A1 | 8/2012 | Wang et al. |
| 2013/0060122 A1 | 3/2013 | Zharov |

FOREIGN PATENT DOCUMENTS

| | | |
|---|---|---|
| WO | 2012/085751 A1 | 6/2012 |
| WO | 2013-053042 A1 | 4/2013 |

OTHER PUBLICATIONS

Skyba et al. ("Direct in vivo visualization of intravascular destruction of microbubbles by ultrasound and its local effects on tissue", 1998).*
Huynh et al. ("Porphyrin shell microbubbles with intrinsic ultrasound and photoacoustic properties", J. of American chemical society, 2012), hereinafter "Huynh".*
Yamabe et al. (J. controlled release 2003,89,429-436) hereinafter "Yamabe".*
International Search Report dated Oct. 27, 2014 issued in International Patent Application No. PCT/KR2014/006568.
Kim, C.; Favazza, C.; Wang, L. V., In vivo photoacoustic tomography of chemicals: high-resolution functional and molecular optical imaging at new depths. Chemical reviews 2010, 110 (5), 2756-82.
Beard, P., Biomedical photoacoustic imaging. Interface focus 2011, 1 (4), 602-31.
Wang, L. V.; Hu, S., Photoacoustic tomography: in vivo imaging from organelles to organs. Science 2012, 335 (6075), 1458-62.
Yao, J.; Xia, J.; Maslov, K. I.; Nasiriavanaki, M.; Tsytsarev, V.; Demchenko, A. V.; Wang, L. V., Noninvasive photoacoustic computed tomography of mouse brain metabolism in vivo. NeuroImage 2013, 64, 257-66.
Laufer, J.; Johnson, P.; Zhang, E.; Treeby, B.; Cox, B.; Pedley, B.; Beard, P., In vivo preclinical photoacoustic imaging of tumor vasculature development and therapy. Journal of biomedical optics 2012, 17 (5), 056016.
Laufer, J.; Norris, F.; Cleary, J.; Zhang, E.; Treeby, B.; Cox, B.; Johnson, P.; Scambler, P.; Lythgoe, M.; Beard, P., In vivo photoacoustic imaging of mouse embryos. Journal of biomedical optics 2012, 17 (6), 061220.
Zemp, R. J.; Song, L.; Bitton, R.; Shung, K. K.; Wang, L. V., Realtime photoacoustic microscopy of murine cardiovascular dynamics. Optics express 2008, 16 (22), 18551-6.
Kim, C.; Erpelding, T. N.; Jankovic, L.; Wang, L. V., Performance benchmarks of an array-based hand-held photoacoustic probe adapted from a clinical ultrasound system for non-invasive sentinel lymph node imaging. Philosophical transactions. Series A, Mathematical, physical, and engineering sciences 2011, 369 (1955).
Kim, C.; Song, K. H.; Gao, F.; Wang, L. V., Sentinel lymph nodes and lymphatic vessels: noninvasive dual-modality in vivo mapping by using indocyanine green in rats—volumetric spectroscopic photoacoustic imaging and planar fluorescence imaging. Radiology 2010, 255 (2), 442-50.
Wang, B.; Zhao, Q.; Barkey, N. M.; Morse, D. L.; Jiang, H., Photoacoustic tomography and fluorescence molecular tomography: a comparative study based on indocyanine green. Medical physics 2012, 39 (5), 2512-7.
Morgounova, E.; Shao, Q.; Hackel, B. J.; Thomas, D. D.; Ashkenazi, S., Photoacoustic lifetime contrast between methylene blue monomers and self-quenched dimers as a model for dual-labeled activatable probes. Journal of biomedical optics, May 2013, 18 (5), 56004.
Cai, X.; Li, W.; Kim, C. H.; Yuan, Y.; Wang, L. V.; Xia, Y., In vivo quantitative evaluation of the transport kinetics of gold nanocages in a lymphatic system by noninvasive photoacoustic tomography. ACS nano 2011, 5 (12), 9658-67.
Kim, C.; Song, H. M.; Cai, X.; Yao, J.; Wei, A.; Wang, L. V., In vivo photoacoustic mapping of lymphatic systems with plasmon-resonant nanostars. Journal of materials chemistry 2011, 21 (9), 2841-2844.
Jokerst, J. V.; Cole, A. J.; Van de Sompel, D.; Gambhir, S. S., Gold nanorods for ovarian cancer detection with photoacoustic imaging and resection guidance via Raman imaging in living mice. ACS nano 2012, 6 (11), 10366-77.
Lovell, J. F.; Jin, C. S.; Huynh, E.; Jin, H.; Kim, C.; Rubinstein, J. L.; Chan, W. C.; Cao, W.; Wang, L. V.; Zheng, G., Porphysome nanovesicles generated by porphyrin bilayers for use as multimodal biophotonic contrast agents. Nature materials 2011, 10 (4), 324-32.
Zha, Z.; Deng, Z.; Li, Y.; Li, C.; Wang, J.; Wang, S.; Qu, E.; Dai, Z., Biocompatible polypyrrole nanoparticles as a novel organic photoacoustic contrast agent for deep tissue imaging. Nanoscale 2013, 5 (10), 4462-7.
Kim, C.; Erpelding, T. N.; Jankovic, L.; Pashley, M. D.; Wang, L. V., Deeply penetrating in vivo photoacoustic imaging using a clinical ultrasound array system. Biomedical optics express 2010, 1 (1), 278-284.
Kim, C.; Erpelding, T. N.; Maslov, K.; Jankovic, L.; Akers, W. J.; Song, L.; Achilefu, S.; Margenthaler, J. A.; Pashley, M. D.; Wang, L. V., Handheld array-based photoacoustic probe for guiding needle biopsy of sentinel lymph nodes. Journal of biomedical optics 2010, 15 (4), 046010.
Wilson, S. R.; Burns, P. N., Microbubble-enhanced US in body imaging: what role Radiology Oct. 2010, 257 (1), 24-39.
Lanza, G. M.; Wickline, S. A., Targeted ultrasonic contrast agents for molecular imaging and therapy. Current problems in cardiology 2003, 28 (12), 625-53.
Song, J.; Qi, M.; Kaul, S.; Price, R. J., Stimulation of arteriogenesis in skeletal muscle by microbubble destruction with ultrasound. Circulation 2002, 106 (12), 1550-1555.
Kim, C.; Qin, R.; Xu, J. S.; Wang, L. V.; Xu, R., Multifunctional microbubbles and nanobubbles for photoacoustic and ultrasound imaging. Journal of biomedical optics 2010, 15 (1), 010510.
Wang, Y. H.; Liao, A. H.; Chen, J. H.; Wang, C. R.; Li, P. C., Photoacoustic/ultrasound dual-modality contrast agent and its application to thermotherapy. Journal of biomedical optics 2012, 17 (4), 045001.
Wilson, K.; Homan, K.; Emelianov, S., Biomedical photoacoustics beyond thermal expansion using triggered nanodroplet vaporization for contrast-enhanced imaging. Nature communications 2012, 3, 618.
Huynh, E.; Lovell, J. F.; Helfield, B. L.; Jean, M.; Kim, C.; Goertz, D. E.; Wilson, B. C.; Zheng, G., Porphyrin shell microbubbles with intrinsic ultrasound and photoacoustic properties. Journal of the American Chemical Society 2012, 134 (40), 16464-7.
Goertz, D. E.; de Jong, N.; van der Steen, A. F., Attenuation and size distribution measurements of Definity and manipulated Definity populations. Ultrasound in medicine & biology 2007, 33 (9), 1376-88.
Kim, C.; Jeon, M.; Wang, L. V., Nonionizing photoacoustic cystography in vivo. Optics letters 2011, 36 (18), 3599-601.
Gorce, J. M.; Arditi, M.; Schneider, M., Influence of bubble size distribution on the echogenicity of ultrasound contrast agents: a study of SonoVue. Investigative radiology 2000, 35 (11), 661-71.

(56) References Cited

OTHER PUBLICATIONS

Sarkar, K.; Shi, W. T.; Chatterjee, D.; Forsberg, F., Characterization of ultrasound contrast microbubbles using in vitro experiments and viscous and viscoelastic interface models for encapsulation. The Journal of the Acoustical Society of America 2005, 118 (1), 539-50.
Ermilov, S. A.; Khamapirad, T.; Conjusteau, A.; Leonard, M. H.; Lacewell, R.; Mehta, K.; Miller, T.; Oraevsky, A. A., Laser optoacoustic imaging system for detection of breast cancer. Journal of biomedical optics 2009, 14 (2), 024007.
Jiao, S.; Jiang, M.; Hu, J.; Fawzi, A.; Zhou, Q.; Shung, K. K.; Puliafito, C. A.; Zhang, H. F., Photoacoustic ophthalmoscopy for in vivo retinal imaging. Optics express 2010, 18 (4), 3967-72.
Yao, J.; Maslov, K. I.; Wang, L. V., In vivo photoacoustic tomography of total blood flow and potential imaging of cancer angiogenesis and hypermetabolism. Technology in cancer research & treatment 2012, 11 (4), 301-7.
Extended European Search Report dated Mar. 28, 2017 issued in European Patent Application No. 14829213.9.
E. Huynh, et al., "Porphyrin Shell Microbubbles with Intrinsic Ultrasound and Photoacoustic Properties," Journal of the American Chemical Society, 2012, vol. 134, pp. 16464-16467.
Y. Wang, et al., "Thermotherapy with a photoacoustic/ultrasound dual-modality agent," Proc. of SPIE, vol. 7899, 2011, pp. 1-5.
Korean Office Action dated Feb. 12, 2020 issued in Korean Patent Application No. 10-2013-0085759 (with English ranslation).

\* cited by examiner

FIG. 2F

| MICROBUBBLES CONCENTRATION | | | |
|---|---|---|---|
| 1 | 0 mg/mL | 2 | 0.05 mg/mL |
| 3 | 0.1 mg/mL | 4 | 0.15 mg/mL |
| 5 | 0.2 mg/mL | 6 | 0.25 mg/mL |

\* METHYLENE BLUE CONCENTRATION, 15 mM

FIG. 3F

| METHYLENE BLUE CONCENTRATION | | | |
|---|---|---|---|
| 1 | 0 mM | 2 | 1 mM |
| 3 | 5 mM | 4 | 10 mM |
| 5 | 15 mM | 6 | 20 mM |

METHYLENE BLUE CONCENTRATION, 0.1 mM

Microbubbles concentration: 0.1 mg/mL
Methylene blue concentration : 15 mM

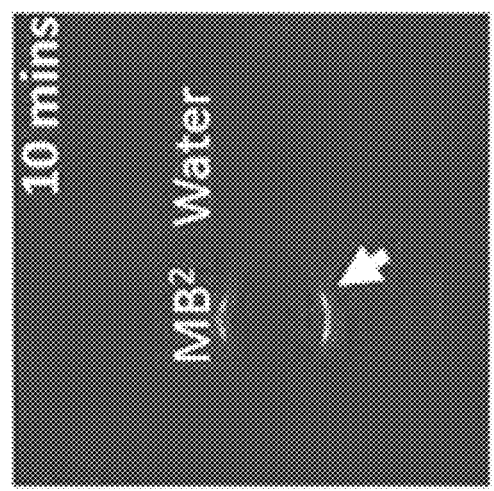
FIG. 5A
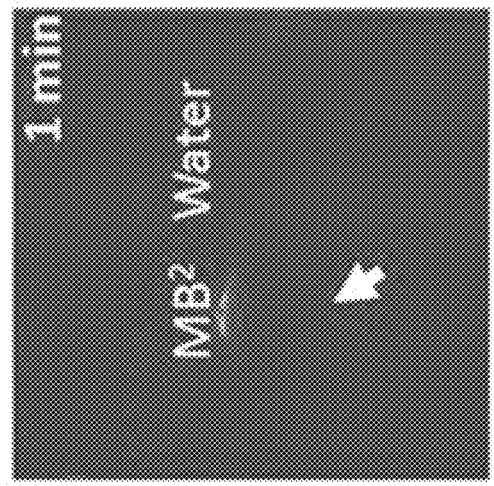
FIG. 5B
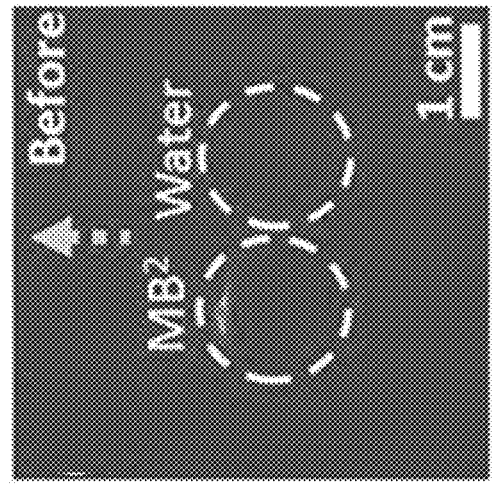
FIG. 5C
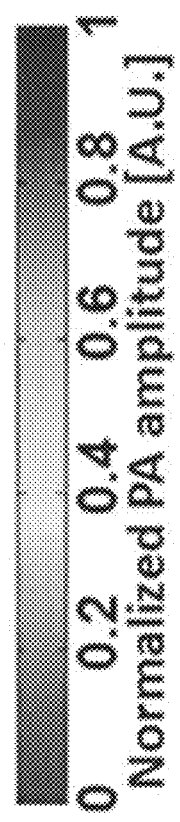

APPARATUS AND METHOD FOR COMBINED PHOTOACOUSTIC AND ULTRASOUND DIAGNOSIS

RELATED APPLICATIONS

This application claims the benefit of Korean Patent Application No. 10-2013-0085759, filed on Jul. 21, 2013, in the Korean Intellectual Property Office, the disclosure of which is incorporated herein in its entirety by reference.

BACKGROUND

1. Field

The present disclosure relates to ultrasound image diagnosis and photoacoustic image diagnosis, and in particular, to an apparatus and method for combined photoacoustic and ultrasound diagnosis.

Photoacoustic imaging provides strong optical absorption contrast and high ultrasound resolution even in deep tissues. The principle of photoacoustic imaging is as follows: the local heat deposition following short laser irradiation pulses generates acoustic waves, and then the propagated waves are detected by conventional ultrasound (US) imaging scanners.

Photoacoustic imaging has been significantly investigated in cancers, brains, hearts, and eyes of small animals. Additionally, thanks to the natural fusion of light excitation and ultrasound detection, photoacoustic imaging system have been easily merged with existing ultrasound imaging system following minor modifications (for example, muting of ultrasound transmission and collection of wireless radiofrequency data). Because the integrated system has shared acoustic detectors, they present the advantages of conventional ultrasound imaging system, such as portability and real-time imaging capability.

At the same time, contrast agents for both imaging modalities have been significantly explored to enhance detection sensitivities and specificities. For example, optically absorbing organic dyes, plasmonic gold nanostructures, and organic nanoparticles have been developed for photoacoustic imaging in various biological applications. From a clinical point of view, biocompatibility (i.e., non-toxicity) and biodegradability of those nanoparticles for PA imaging have not been meaningfully studied, and thus safety is an ongoing issue as photoacoustic moves towards clinical application.

So far, clinically approved dyes (i.e., methylene blue and indocyanine green) have the highest chance to be chosen as clinical photoacoustic contrast agents. Methylene blue is currently being investigated as a photoacoustic lymph node tracer in breast cancer.

For ultrasound imaging, microbubbles filled with fluorinated gases are routinely used in clinical practices to map blood flow in hearts, livers, and kidneys. Preclinically, microbubbles have been tested for molecular ultrasound imaging, ultrasound-guided drug delivery, etc.

Furthermore, dual-functional contrast agents for simultaneous photoacoustic and ultrasound imaging have recently been reported. Examples of such dual-functional contrast agents are ink-encapsulated micro- or nano-bubbles [13]; gold nanorods encapsulated-human serum albumin shelled microbubbles [14]; and liquid perfluorocarbon nanodroplets with plasmonic nanoparticles encapsulated therein [15].

SUMMARY

According to the present disclosure, a microbubble used as a contrast agent for ultrasound imaging may burst by means of high voltage ultrasound, and the burst microbubble may effectively act as a contrast agent for photoacoustic imaging. Based on this point, the present disclosure provides a new apparatus and method for combined photoacoustic and ultrasound diagnosis.

Additional aspects will be set forth in part in the description which follows and, in part, will be apparent from the description, or may be learned by practice of the presented embodiments.

An embodiment of a combined photoacoustic and ultrasound diagnosis method according to an aspect of the present disclosure includes transmitting a first ultrasound signal having a low MI to a subject to which a contrast agent having microbubbles has been administered, detecting an echo signal that is generated by the reflection of the first ultrasound signal by microbubbles, and displaying an ultrasound image produced based on the echo signal;

transmitting a second ultrasound signal having a high MI to the subject to burst the microbubbles to form microbubble flakes; and irradiating a laser signal to the subject, detecting a photoacoustic signal generated due to the microbubble flakes stimulated by the laser signal, and then, displaying a photoacoustic image produced based on the photoacoustic signal.

An embodiment of a combined photoacoustic and ultrasound diagnostic apparatus according to an aspect of the present disclosure includes a laser irradiation unit for irradiating a laser signal to a subject;

an ultrasound signal transducer for transmitting a first ultrasound signal having a low MI to the subject, detecting an echo signal generated due to the first ultrasound signal reflected by microbubbles in the subject, transmitting a second ultrasound signal having high MI to the subject to burst the microbubbles to form microbubble flakes, and detecting a photoacoustic signal generated by the microbubble flakes stimulated by the laser signal;

an image processing unit for producing a photoacoustic image based on the photoacoustic signal and an ultrasound image based on the echo signal; and a display unit for displaying the photoacoustic image and the ultrasound image.

BRIEF DESCRIPTION OF THE DRAWINGS

These and/or other aspects will become apparent and more readily appreciated from the following description of the embodiments, taken in conjunction with the accompanying drawings in which:

FIGS. 2A-2F shows (2A) photoacoustic imaging of methylene blue-colored microbubble aqueous solutions with various concentrations of microbubbles at a fixed methylene blue concentration (15 mM), (2B) ultrasound imaging of methylene blue-colored microbubble aqueous solutions with various concentrations of microbubbles at a fixed methylene blue concentration (15 mM), (2C) a relationship between quantified photoacoustic signals and a microbubble concentration, (2D) a relationship between a quantified ultrasound signal and a microbubble concentration, (2E) photographs of samples, and (2F) concentrations of microbubbles and methylene blue in 6 samples;

FIGS. 3A-3F shows (3A) photoacoustic imaging of methylene blue-colored microbubble aqueous solutions with various concentrations of methylene blue at a fixed microbubble concentration (0.1 mg/ml), (3B) ultrasound imaging of methylene blue-colored microbubble aqueous solutions with various concentrations of methylene blue at a fixed microbubble concentration (0.1 mg/ml), (3C) a relationship between quantified photoacoustic signals and a methylene blue concentration, (3D) a relationship between quantified ultrasound signals and methylene blue concentration, (3E) photographs of samples, and (3F) concentrations of microbubbles and methylene blue in 6 samples;

FIGS. 5A-5D shows (5A) photoacoustic imaging of a methylene blue-colored microbubble aqueous solution before the applying of high-voltage ultrasound generated by a clinical ultrasound array, (5B) a photoacoustic image one minute after the applying, (5C) a photoacoustic image ten minutes after the applying, and (5D) a relationship between quantified photoacoustic signals and an ultrasound applying time;

DETAILED DESCRIPTION

Figure 1A:
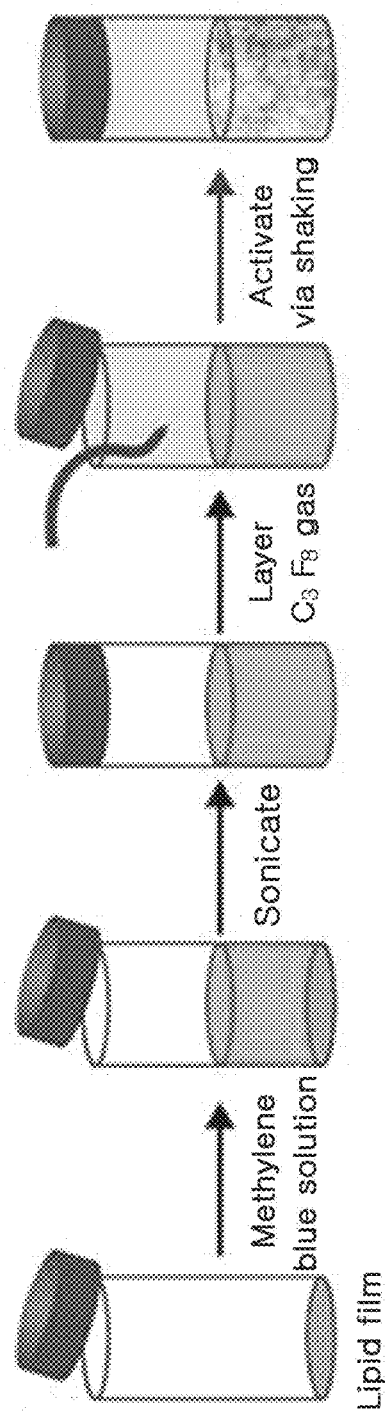
FIGS. 1A-1F illustrates a process of synthesizing methylene blue-colored microbubbles, and shows physical/optical properties of methylene blue-colored microbubbles.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. Expressions such as "at least one of," when preceding a list of elements, modify the entire list of elements and do not modify the individual elements of the list.

Figure 6:
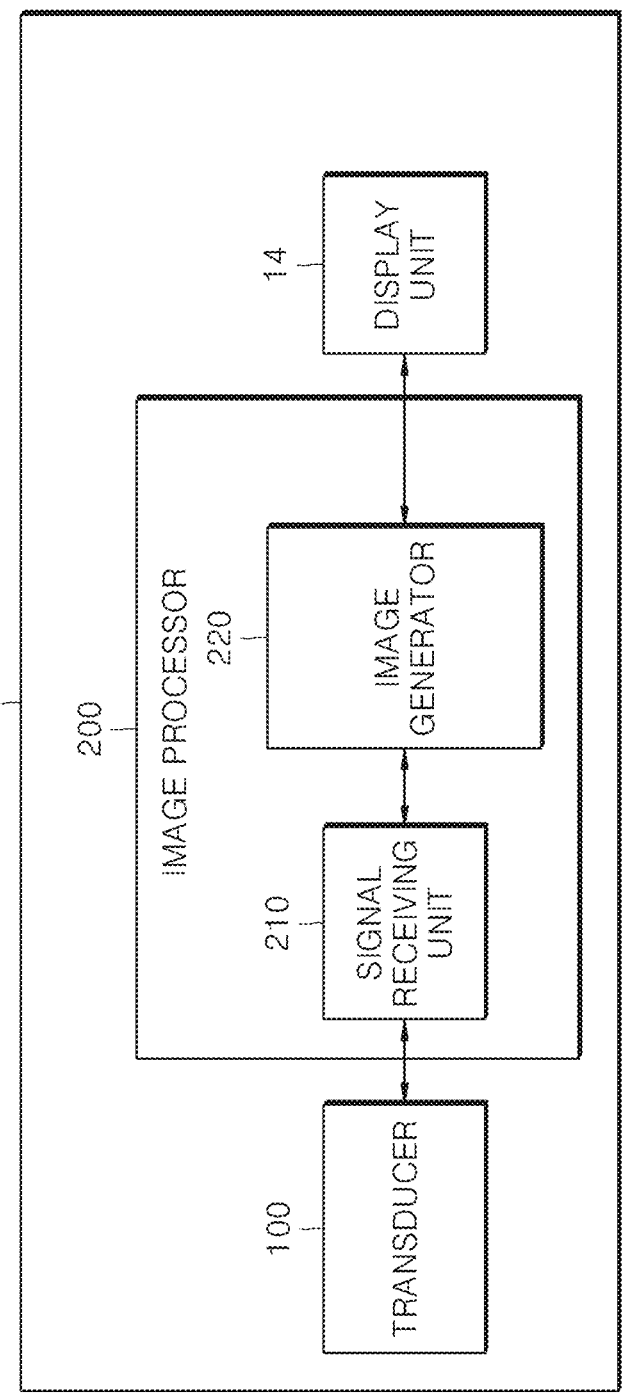
FIG. 6 is a block diagram of an embodiment of a combined photoacoustic and ultrasound diagnostic apparatus provided according to an aspect of the present disclosure.
Figure 7:
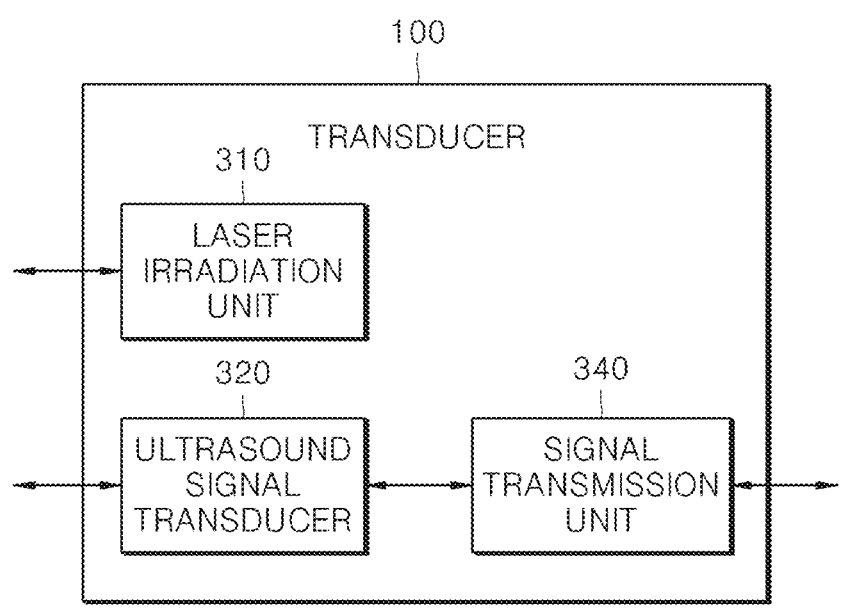
FIG. 7 is a block diagram of a transducer of the embodiment of a combined photoacoustic and ultrasound diagnostic apparatus of FIG. 6.

Hereinafter, referring to FIGS. 6 and 7, a combined photoacoustic and ultrasound diagnostic apparatus according to an embodiment of the present disclosure will be described in detail. FIG. 6 is a block diagram of an example of a combined photoacoustic and ultrasound diagnostic apparatus 10 provided according to another aspect of the present disclosure. The combined photoacoustic and ultrasound diagnostic apparatus 10 includes a transducer (also referred to as a probe) 100, a display unit 14, and an image processor 200. FIG. 7 is a block diagram of the transducer 100 of FIG. 6.

The transducer 100 may include a laser irradiation unit 310, an ultrasound signal transducer 320, and a signal transmission unit 340.

The ultrasound signal transducer 320 may transmit a first ultrasound signal having a low mechanical index (MI) to a subject. An echo signal may be generated due to reflection of the first ultrasound signal by microbubbles. In some embodiments, the ultrasound signal transducer 320 may also transmit a second ultrasound signal having a high MI to a subject. The second ultrasound signal causes microbubbles in the subject to burst. Once microbubbles burst, a filling material (for example, a filling gas or a drug) inside the microbubbles may be released into the subject, and the burst microbubbles, that is, microbubble flakes, may be formed.

The first ultrasound signal may have a low MI. MI refers to an ultrasound metric that is determined by using the peak negative pressure and a center frequency of an ultrasound wave. MI also indicates a degree of a bio-effect caused due to ultrasound, and an ultrasound signal having a higher MI leads to a higher bio-effect. The Food and Drug Administration (FDA) of the United States of America requires that in ultrasound diagnosis, an MI value must not exceed 1.9. The first ultrasound signal may have, for example, a low MI that is equal to or greater than about 0.2 and less than about 0.5. Within this low MI range, microbubbles used as a contrast agent do not burst. Accordingly, microbubbles in the subject to which the first ultrasound signal has been transmitted may effectively reflect the first ultrasound signal, thereby generating an echo signal.

The second ultrasound signal may have a high MI. The second ultrasound signal may have, for example, a high MI of about 0.5 to about 1.9. Within this high MI range, microbubbles used as a contrast agent effectively burst. Accordingly, a filling material inside of the microbubbles is released as the microbubbles in the subject to which the second ultrasound signal has been transmitted burst, and microbubble flakes are formed.

The laser irradiation unit 310 irradiates a subject with a laser signal. The laser signal transmitted by the laser irradiation unit 310 may be any one of various optical stimulation signals. The laser irradiation unit 310 may preset the intensity of a laser to be transmitted. When the laser irradiation unit 310 irradiates a laser having an intensity that is equal to or higher than a predetermined value to a subject, microbubble flakes in the subject absorb energy via light from the laser. Once microbubble flakes absorb energy, the microbubble flakes thermally expand, and due to the thermal expansion, ultrasound signals are generated. This is called a photoacoustic effect, and an ultrasound signal generated due to thermal expansion is referred to as a photoacoustic signal. In other embodiments, the laser irradiation unit 310 may be physically separate from the transducer 100 to be disposed outside the transducer 100.

The ultrasound signal transducer 320 detects echo signals that are generated due to microbubbles inside the subject to which the first ultrasound signal has been transmitted and photoacoustic signals that are generated due to microbubble flakes inside the subject to which a laser signal has been irradiated. The signal transmission unit 340 transmits the echo signals and photoacoustic signals detected by the ultrasound signal transducer 320 to the image processor 200.

The image processor 200 receives a scan signal (that is, an echo signal and a photoacoustic signal) obtained when the transducer 100 scans the subject, and performs converting the scan signal into an image which can be displayed. The image processor 200 includes a signal receiving unit 210 and an image generator 220. The signal receiving unit 210 receives an echo signal and a photoacoustic signal transmitted from the transducer 100. The signal receiving unit 210 transmits the received echo signal and photoacoustic signal to the image generator 220. The image generator 220 generates images respectively corresponding to each of the echo signal and the photoacoustic signal and then, transmits the images to the display unit 14.

The display unit 14 displays the images transmitted by the image processor 200. The display unit 14 may include, for example, at least one selected from a liquid crystal display (LCD), an organic light-emitting diode (OLED), a flexible display, and a 3-dimensional (3D) display. Also, the display unit 14 is not limited thereto, and may be any one of various devices that display an image of a subject.

Figure 8:
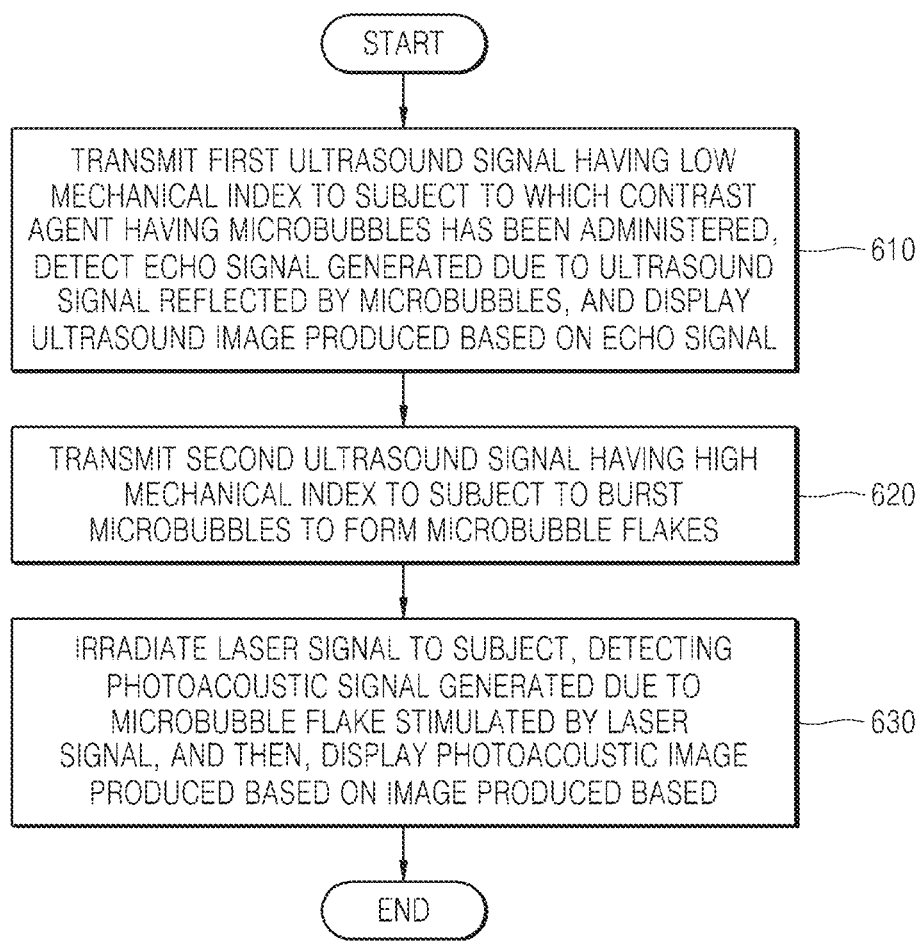
FIG. 8 is a flow chart showing an embodiment of a combined photoacoustic and ultrasound diagnostic method provided according to another aspect of the present disclosure.

Hereinafter, referring to FIG. 8, a combined photoacoustic and ultrasound diagnostic method according to an embodiment of the present disclosure will be described in detail. FIG. 8 is a flow chart showing a combined photoacoustic and ultrasound diagnostic method provided according to another aspect of the present disclosure. The flowchart of FIG. 8 illustrates operations that are time-serially performed by the transducer 100, the image processor 200, and the display unit 14 illustrated in FIG. 6. Accordingly, even when not described hereinafter, elements described above in connection with FIG. 6 may be applied to the flowchart of FIG. 8.

In operation 610, a first ultrasound signal having a low MI is transmitted to a subject to which a contrast agent having microbubbles has been administered, and a first echo signal that is generated due to reflection of the first ultrasound signal by microbubbles is detected, and an ultrasound image produced based on the first echo signal is displayed. The transmission of the first ultrasound signal and the detection of the first echo signal may be performed by the ultrasound signal transducer 320. The displaying of a ultrasound image may be performed by the display unit 14. The first ultrasound signal may have a low MI of, for example, about 0.2 to about 0.5. For example, by using the ultrasound image displayed in operation 610, microbubbles containing a drug that is to be delivered to a particular organ in the subject may be monitored to determine whether the microbubbles reach the particular organ.

In operation 620, a second ultrasound signal having a high MI is transmitted to the subject to burst the microbubbles to form microbubble flakes. The transmission of the second ultrasound signal may be performed by the ultrasound signal transducer 320. The second ultrasound signal may have, for example, a high MI of about 0.5 to about 1.9. Since the second ultrasound signal having a high intensity is transmitted to the subject, the ultrasound signal transducer 320 may detect a second echo signal generated due to the reflection by a wall of the particular organ. Accordingly, an ultrasound image corresponding to the wall of the particular organ may be continuously displayed by the display unit 14. However, as the transmission of the second ultrasound signal continues, microbubbles may continuously burst, and accordingly, the first echo signal generated due to reflection of the first ultrasound signal by the microbubbles is gradually attenuated. For example, the operation 620 may begin when the arriving of microbubbles, which contain a drug that is to be delivered to a particular organ in the subject, at the particular organ is confirmed via the ultrasound image displayed in operation 610. By doing so, the drug contained in the microbubbles may be effectively delivered to the particular organ.

In operation 630, a laser signal is irradiated to the subject, a photoacoustic signal generated due to thermal expansion of microbubble flakes stimulated by the laser signal is detected, and then, a photoacoustic image produced based on the photoacoustic signal is displayed. The transmission of the laser signal may be performed by the laser irradiation unit 310. The detecting of the photoacoustic signal may be performed by the ultrasound signal transducer 320. The displaying of the photoacoustic image may be performed by the display unit 14. For example, the operation 630 may be performed when or after the operation 620 begins. Since in operation 620, microbubbles burst due to the second ultrasound signal, the first echo signal generated due to reflection of the first ultrasound signal by microbubbles is attenuated and thus, the ultrasound imaging may fail to track the behavior of microbubbles. However, in operation 630, photoacoustic signals generated due to the bursting of the microbubbles, that is, microbubble flakes, are gradually intensified due to the increase in the number of microbubble flakes so that the behavior of microbubble flakes becomes trackable by photoacoustic imaging. Accordingly, the use of microbubbles and the application of combined ultrasound imaging and photoacoustic imaging enable an embodiment of a diagnostic method that continuously tracks the behavior of microbubble flakes of microbubbles that have been burst to deliver a drug. The detection of photoacoustic signals generated due to microbubble flakes may lead to an immediate indication that a drug is released from the inside of microbubbles. Additionally, the detection of photo acoustic signals may lead to location information as high accurate as when the spatial resolving power of ultrasound equipments is used, indicating that a drug effectively permeates into the target organ or tissue.

In an embodiment, a microbubble may be a colored microbubble including a lipid shell colored with dye; and a filling gas encapsulated by the lipid shell. The colored microbubble may be effectively used as a double modality contrast agent for ultrasound and photoacoustic imaging. According to the present disclosure, the photoacoustic signals were significantly suppressed according to the increase of the colored microbubble concentration in a colored microbubble suspension (with fixed dye concentration). Also, even when the concentration of dye increases (a concentration of microbubble is fixed), ultrasound intensity does not change. Also, high powered ultrasound generated by, for example, a clinical ultrasound imaging scanner may be used to burst the colored microbubble, and accordingly, dramatically restore photoacoustic signals (up to about 817 times). This is a truly innovative mechanism to modulate photoacoustic signal generation. Conventionally, one or more parameters with respect to the initial photoacoustic amplitude (for example, Grueneisen coefficient, heat conversion efficiency, optical absorption coefficient, or optical induction) within an object are required to be adjusted to control the photoacoustic signals. However, by using microbubbles having dye-colored lipid shells, these parameters are not needed for consideration any more. From a clinical point of view, dye, such as methylene blue, and lipid shell have been widely used in clinical practices. Accordingly, the colored microbubble has very high stability. Also, even in consideration of functionality, the colored microbubble has direct translationabilities into a clinical photoacoustic imaging system. Accordingly, the colored microbubble enables effective embodiment of the combined photoacoustic and ultrasound imaging system.

The dye absorbs incident light. The dye that has absorbed incident light causes heat deposit of the dye and the shell. Due to the heat deposit, the dye or the shell generates a sound wave. The dye may absorb incident light having a wavelength of, for example, about 500 nm to about 1,300 nm. The sound wave generated from a dye, a dye-colored shell, or a flake of the dye-colored shell may be in a range of, for example, about 1 MHz to about 50 MHz. The sound wave generated from a dye, a dye-colored shell, or a flake of the dye-colored shell may be detected by using, for example, an ultrasound scanner.

The dye may be, for example, azure blue, evans blue, indocyanine green, brilliant blue, nile blue, methylene blue, or a combination thereof. These dyes may have non-toxicity and biodegradability.

A degree of coloring a shell may be adjusted by, for example, controlling the concentration of dye in a dye solution used to hydrate lipid used to prepare the shell. When the concentration of dye in a dye solution used to hydrate lipid is too low, the dye-induced photoacoustic signal may be less produced, and thus, detection thereof may be difficult. When the concentration of dye in a dye solution used to hydrate lipid is too high, the concentration exceeds a maximum concentration for which biosafety is guaranteed and thus, safety-related problems may occur. A concentration of dye in a dye solution used to hydrate lipid may be in a range of, for example, about 0.5 mM to about 20 mM. In an embodiment, for example, a concentration of dye in a dye solution used to hydrate lipid may be about 15 mM. In an embodiment, for example, dye may be methylene blue, and a concentration of dye in a dye solution used to hydrate lipid may be in a range of about 0.5 mM to about 20 mM. In an embodiment, for example, dye may be methylene blue, and a concentration of dye in a dye solution used to hydrate lipid may be in a range of may be about 15 mM.

A solvent for the dye solution may be, for example, water, an electrolytic aqueous solution, or a combination thereof. A specific example of the solvent for the dye solution may be PBS.

The coloring of lipid may be performed by immersing lipid in a dye solution.

Lipid may be, for example, triglyceride that is a fatty acid ester of glycerol that is an alcohol, a phosphoglyceride (phospholipid) that is a fatty acid ester of glycerol and a phosphoric acid, sphingolipid that is a complex lipid induced from an alcohol, such as sphingosine, steroid, such as cholesterol, carotinoid, prostaglandin, or a mixture thereof. In an embodiment, lipid may include phospholipid. Phospholipid may spontaneously form a single layer having high self-orientation at a gas (air)-water interface, and accordingly, when in contact with gas bubbles, a water-repellent acyl chains are oriented toward the inside of bubbles and a hydrophilic head groups are oriented toward a solution, thereby effectively forming a shell. Detailed examples of phospholipid are, for example, 1,2-dipalmitoyl-sn-glycero-3-phosphatidic acid (DPPA); 1,2-dipalmitoyl-sn-glycero-3-phosphatidylcholine (DPPC); 1,2-distearoyl-sn-glycero-3-phosphocholine (DSPC); 1,2-dimyristoyl-sn-glycero-3-phosphocholine (DMPC); 1,2-dibehenoyl-sn-glycero-3-phosphocholine (DBPC); 1,2-diarachidoyl-sn-glycero-3-phosphatidylcholine (DAPC); 1,2-dilignoceroyl-sn-glycero-3-phosphatidylcholine (DLgPC); 1,2-dipalmitoyl-sn-glycero-3-[phosphor-rac-(1-glycerol)] (DPPG); and a mixture thereof.

The dye-colored lipid shell acts as a container for accommodating a filler therein, for example, filling gas and/or drug. A microbubble having a shell encapsulating filling gas may reflect ultrasound. A microbubble having a shell encapsulating a drug therein may act as a drug carrier.

The shape of the shell is not limited, and for example, the shell may be spherical. When a particle diameter of the shell is too small, scattering due to ultrasound may be weak and thus, ultrasound imaging may be difficult. When a particle diameter of the shell is too great, it is difficult to retain the shape of the shell, and when the shell is injected in vivo by using, for example, a syringe, the shell may burst. A particle diameter of the shell may be in a range of, for example, about 0.5 µm to about 10 µm.

A thickness of a wall of the shell may be in a range of, for example, about 1 nm to about 200 nm. Since a filling gas bubble can hardly retain the physical shape of a microbubble, a shell having an appropriate thickness is required. The thickness of the shell may vary according to a material used to form a shell, such as a surfactant, a lipid, a protein, a polymer, or a combination thereof.

The shell encapsulates filling gas. The filling gas may prevent the shell from shriveling. Also, a microbubble having the shell encapsulating filling gas may reflect ultrasound. The filling gas may be a biologically inactive gas. Specific examples of the filling gas are perfluorocarbon, sulphur hexafluoride, perfluoromethane, perfluoroethane, perfluoropropane, perfluorobutane, perfluoropentane, perfluorohexane, perfluoroheptane, perfluorooctane, perfluorononane, perluorodecane, perfuorobenzene, perfluorotriethylamine, perfluorooctylbromide, and a mixture thereof.

Embodiments of a microbubble including a dye-colored lipid shell; and filling gas encapsulated by the lipid shell may act as a contrast agent for ultrasound imaging. Also, embodiments of the microbubble may burst due to high-voltage ultrasound. When a microbubble according to the present disclosure bursts due to high-voltage ultrasound, a filler, such as filling gas and/or a drug, may be released, and also, a flake of the dye-colored lipid shell may be formed. The flake of the dye-colored lipid shell may substantially increase photoacoustic efficiency of incident light. For example, the flake of the dye-colored lipid shell can generate a photoacoustic signal that is about 817 times stronger than the dye-colored lipid shell which exists in the form of a microbubble. Accordingly, embodiments of the microbubble of the present disclosure, which accompany the bursting due to high-voltage ultrasound, may be very effectively used as a contrast agent for combined ultrasound and photoacoustic imaging. Also, since embodiments of the microbubble of the present disclosure accompany the bursting due to high-voltage ultrasound, a drug contained in the microbubble may be released. Accordingly, embodiments of the microbubble of the present disclosure may act as a drug carrier.

The colored microbubble according to the present disclosure may burst by using ultrasound pulses which may be produced by using a commercially available imaging diagnosis apparatus. In an embodiment, for example, a voltage of about 50 V is applied to a commercially available ultrasound probe to cause the microbubble to burst. In an embodiment, for example, the colored microbubble may burst due to ultrasound that may be produced by applying a voltage pulse of about 50 V (amplitude) or less. In an embodiment, for example, the colored microbubble may burst due to ultrasound that may be produced by applying a voltage pulse of about 20 V (amplitude) to about 50 V (amplitude). In an embodiment, for example, the colored microbubble may burst due to an ultrasound signal having a high mechanical index (MI) of about 0.5 to about 1.9.

Another embodiment of the colored microbubble may further include a drug located inside the shell. The drug may be, for example, an anti-cancer agent, or other various drugs. In the case that the shell is formed of phospholipid, a water-repellent drug that is bindable to water-repellent acyl chains may be loaded, and when a drug is included in a water-repellent other material, the drug may be loaded inside the microbubble.

The colored microbubble may be prepared by using, for example, a method of preparing a microbubble including stirring a dye-colored lipid containing solution in the presence of filling gas.

In other embodiments of the method, the dye-colored lipid-containing solution may further include an emulsifier. The emulsifier may be, for example, N-(methoxypolyethylene glycol 5000 carbamoyl)-1,2-dipalmitoyl-sn-glycero-3-phosphatidylethanolamine (MPEG5000-DPPE), 1,2-dimyristoyl-sn-glycero-3-phosphoethanolamine-N-[methoxy(polyethylene glycol)-2000 (DMPE-PEG2000), 1,2-distearoyl-sn-glycero-3-phosphoethanolamine-N-[methoxy(polyethylene glycol)-2000 (DSPE-PEG2000), Polyoxyethylene 40 stearate (PEG40S), or a combination thereof.

In other embodiments of the method, the dye-colored lipid may be a lipid which is colored by using a dye solution including dye and at least one of glycerol, propylene glycol, phosphate, and sodium chloride.

Example

Preparation of Microbubble Dyed with Methylene Blue

Chemical materials used in this experiment are obtained Sigma Co. unless defined otherwise. In the present example, a microbubble having a methylene blue-colored lipid shell encapsulating octafluoropropane gas (manufacturer: Concorde Specialty Gases Inc., USA) was prepared. The following lipids were obtained from "Avanti Polar lipids Inc., USA": 1,2-dipalmitoyl-sn-glycero-3-phosphate (DPPA; Avanti #830855); 1,2-dipalmitoyl-sn-glycero-3-phosphocholine (DPPC; Avanti #850355); and 1,2-dipalmitoyl-sn-glycero-3-phosphoethanolamine-N-[methoxy(polyethylene glycol)-5000] (MPEG5000; Avanti #880200). Methylene blue was dissolved in PBS (pH=7) to prepare a methylene blue-PBS solution (methylene blue concentration: 20 mM). 1 liter of phosphate-buffered saline (PBS) included 8 g of NaCl, 0.2 g of KCl, 1.44 g of $Na_2HPO_4$, 0.24 g of $KH_2PO_4$, and the balance of water, and a pH thereof was adjusted to 7. DPPA was dissolved in chloroform to prepare a DPPA solution (DPPA concentration: 20 mg/mL), which is then preserved at a temperature of −20° C. DPPC was dissolved in chloroform to prepare a DPPC solution (DPPC concentration: 20 mg/mL), which was then preserved at a temperature of −20° C. MPEG5000 was dissolved in chloroform to prepare a MPEG5000 solution (MPEG5000 concentration: 20 mg/mL), which was then preserved at a temperature of −20° C. Lipid films were prepared at different total concentrations of the lipids while a molar ratio of DPPC:DPPA:MPEG5000 was maintained at 10:1:1.2. Lipid was dissolved in chloroform, and then, the chloroform was evaporated to prepare a lipid film. Lipid was used to prepare, unless explained otherwise, 1 mg/mL of a lipid solution. 750 μl of a methylene blue-PBS solution, 100 μl of propylene glycol (Bioshop Canada # PRO888.1), and 100 μl of glycerol (Bioshop Canada # GLY001.1) were mixed to obtain a dye solution. To hydrate the lipid film with the dye solution, the dye solution and the lipid suspension were loaded into a vial. Octafluoropropane gas was allowed to occupy an upper space of the vial. Then, the vial was sealed, and ultrasound was applied thereto to exchange gas in the solution with octafluoropropane. Then, the upper space of the vial was filled with octafluoropropane gas. Then, the vial was subjected to agitation by using a "vialmix activator" manufactured by "Lantheus Medical Imaging" Co. for 45 seconds, thereby preparing a microbubble having a methylene blue-colored lipid shell.

Evaluation on Physical, Optical, and Acoustic Characteristics of Methylene Blue-Dyed Microbubble After activation, the vial was left for 15 minutes until its temperature dropped to room temperature. Microbubbles were gently mixed for 10 seconds, and then decanted for 2 minutes before extracting a sample from the bottom of the vial. The size distribution and concentration (number of microbubbles per ml) of microbubbles in each of a variety of formulations were measured by using "Coulter Counter Multisizer Z3 (Beckman Coulter Inc.)". Varying volumes 15 μl of microbubbles were extracted and added to 10 mol of "Isoton-II electrolyte solution (Beckman Coulter Inc.)" to obtain a microbubble count in the range of 100,000-300,000. A background count of buffer was taken prior to measurement and subtracted. Dilution was accounted for in the calculation of the microbubble concentration. The number and size distribution were measured using a 30 μm aperture, and thus, it was confirmed that microbubbles had a diameter of about 0.76 to about 18 μM. For each microbubble formulation, three samples were measured and measurement values thereof were averaged. The frequency-dependent attenuation measurements were performed using a narrow-band pulse-echo method similar to that used by "Goertz et al."[see 17]. One transducer (model #595396, 5 MHz, 76 mm focus, 12.7 mm diameter; Olympus NDT Canada Inc., Quebec, Canada) was used to cover a frequency range of about 1.5 to about 12 MHz sampled in 0.5 MHz increments. Each pulse was generated using an arbitrary waveform generator (Tabor Electronics Ltd., Tel Hanan, Israel) and amplified using a power amplifier (model A-150; ENI, Rochester, N.Y., USA). The transducer was calibrated for each frequency using a 75 μm needle hydrophone (model 1544; Precision Acoustics, Dorchester, UK) to deliver a peak negative pressure of 25 kPa at the geometric foci, where the face of an aluminum rod serving as a near-perfect reflector was placed. The received echoes were amplified (model AU1579; Miteq, Hauppauge, N.Y., USA), filtered, and recorded (400 MHz of sampling frequency; Agilent Technologies Inc., Palo Alto, Calif., USA) for further post-process analysis. Echoes were recorded prior to and after contrast agent microbubbles were diluted in the gas-equilibriated saline between the transducer and aluminum reflector. Given the ratio of echo amplitudes pre- and post-contrast agent addition and the length in which ultrasound traveled through the bubbly media, the attenuation per unit length could be calculated at each frequency. Optical absorption spectra of the microbubble contrast agent were recorded in PBS using the indicated dilution using a spectrophotometer (Lamdba 20, PerkinElmer).

Photoacoustic and Ultrasound Imaging Using Methylene Blue-Dyed Microbubble

Two types of combined photoacoustic and ultrasound imaging system were used. The first one was operated with a single-element focused transducer with raster scanning, whereas the other one was modified from a clinical ultrasound array system. Details of the first system are disclosed in reference document 18. Laser pulsing was generated from a controllable laser generator (Surelite OPO PLUS; Continuum; wavelength tuning range: 680 to 1064 nm) pumped by a Q-switched Nd:YAG laser (SLIII-10; Continuum; 532 nm). The pulse width and repetition rate were 5 ns and 10 Hz, respectively. An optical wavelength of 667 nm was used for photoacoustic imaging. Light having this optical wavelength was irradiated to samples through a concave lens, a conical lens, and an optical condenser. A water tray was employed for acoustic coupling. Induced photoacoustic sound waves were sensed by a single-element acoustic transducer (V308; Olympus NDT; 5 MHz center frequency). Then, the photoacoustic signals transferred to a low-noise amplifier (5072PR, Olympus NDT) were recorded by a data acquisition system. In the ultrasound imaging mode, the low-noise amplifier was used as both an ultrasound pulse transmitter and receiver, and the same transducer was used. To form the volumetric data, mechanical raster scanning was used in two transverse directions along the x-y directions. The sample holder had a diameter of 4.5 mm and a depth of 3.2 mm, and was filled with aqueous samples. To investigate the restoration of photoacoustic signals, the photoacoustic and ultrasound signals of the methylene blue-dyed microbubble solution were compared before and after the treatment with ultrasound. Further, to confirm this restoration and investigate the clinical applicability of the mechanism, a clinical photoacoustic imaging scanner was used. 256 channel simultaneous analog-digital converters (ADC) and external triggering capabilities enabled real-time photoacoustic/ultrasound imaging. Conventional ultrasound and photoacoustic images were obtained sequentially, and displayed in the ultrasound imaging monitor. In this regard, structural ultrasound and functional photoacoustic (that is, optical absorption characteristics) images were shown at the same time up to 10 Hz of a PA frame rate. A linear probe with a 7.5 MHz center frequency (Samsung Medison, Seoul, Korea) was used. An OPO laser (Phocus HE, Opotek, Calif., USA) was employed to provide laser pulses with an optical wavelength of 680 nm, a pulse width of 10 ns, and a pulse repetition rate of 10 Hz. A bifurcated optical fiber bundle was used to deliver light to the sample. For the real-time image reconstruction, one-way (receiving mode only) conventional delay-sum beam forming method was employed. One side surface of a rectangular water container was cut opened, and the opened area was covered by a thin transparent window to prevent the leakage of aqueous solutions and enhance acoustic coupling. One optically transparent plastic vial with a diameter of 7 mm was filled with a methylene blue-dyed microbubble solution (microbubble concentration 0.1 mg/ml; methylene blue concentration 15 mM), the other vial was filled with water as a control. Both vials were vertically positioned inside the container which was filled with water. The photoacoustic/ultrasound probe was horizontally positioned with its surface directing the center of the vials. Before microbubbles in the solutions were disturbed, the control photoacoustic image was obtained. Then, the ultrasound transmission voltage increased to 50 V (the typical voltage is 8 V), was delivered to the vials for 60 seconds, and the photoacoustic image was again obtained. This process was repeatedly performed until the methylene blue-dyed microbubble was accumulatively exposed to the high voltage ultrasound for 10 minutes.

Evaluation Results

Figure 1B:
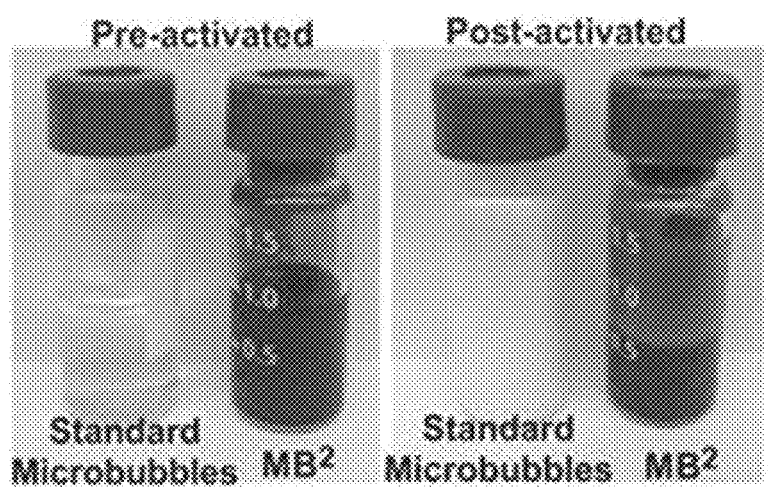
Figure 1C:
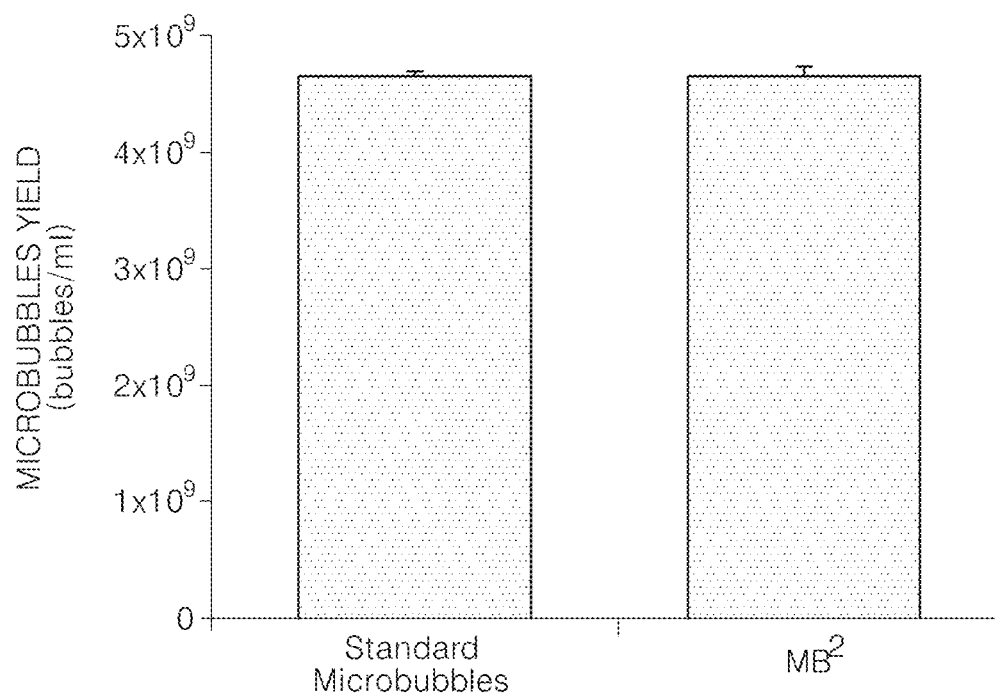
Figure 1D:
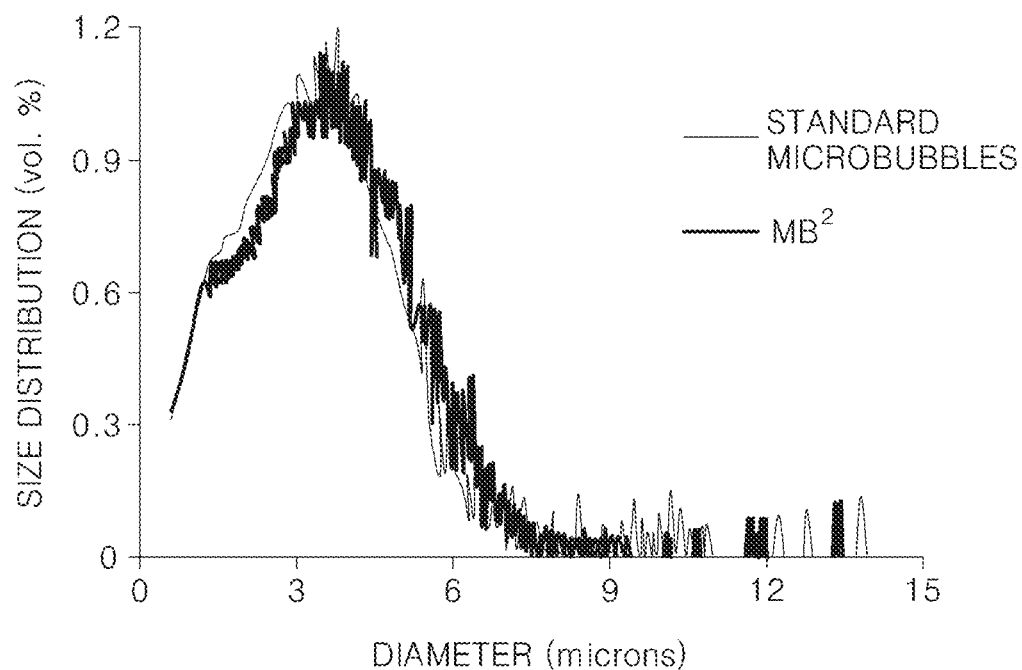
Figure 1E:
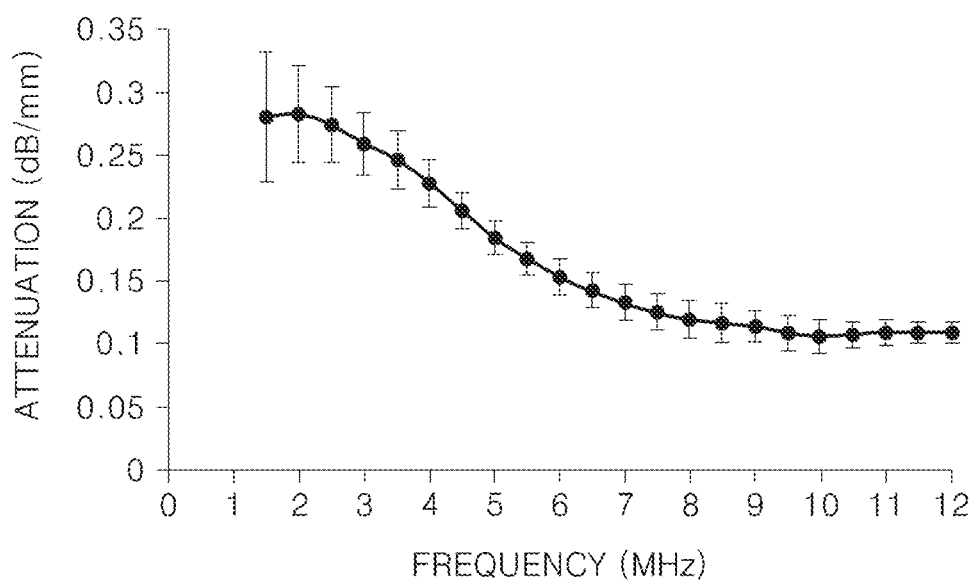
Figure 1F:
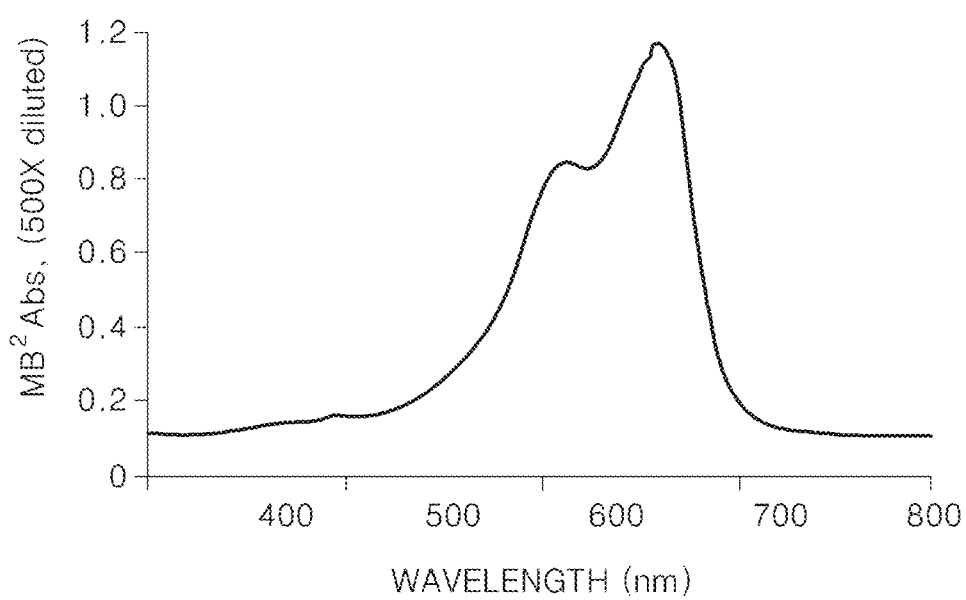
Figure 2A:
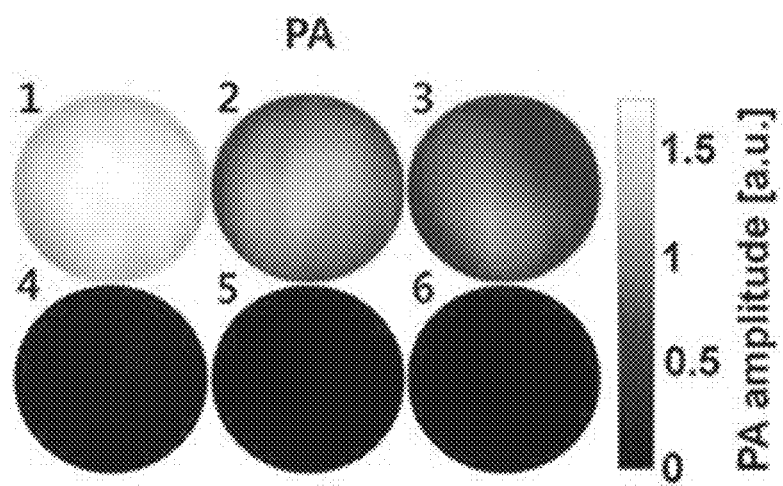
Figure 2B:
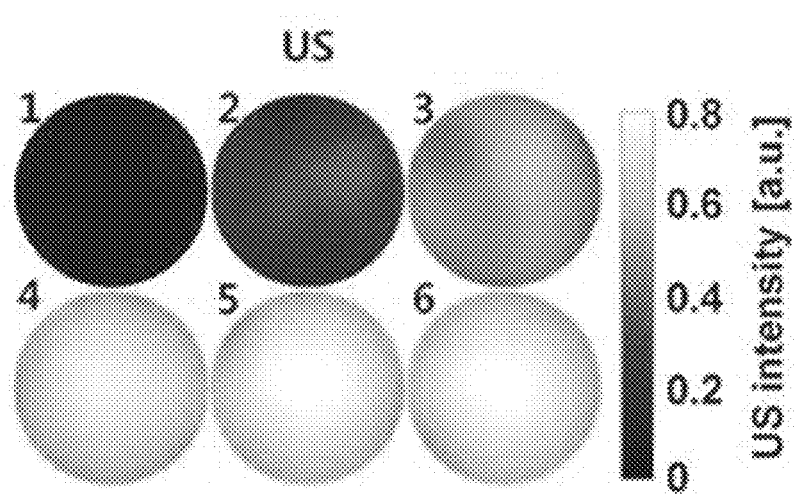
Figure 2C:
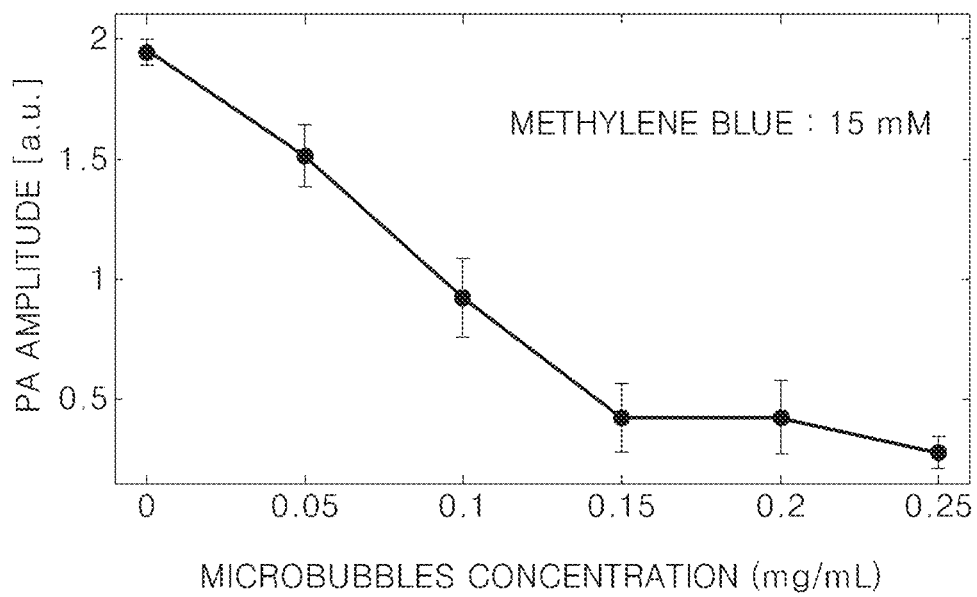
Figure 2D:
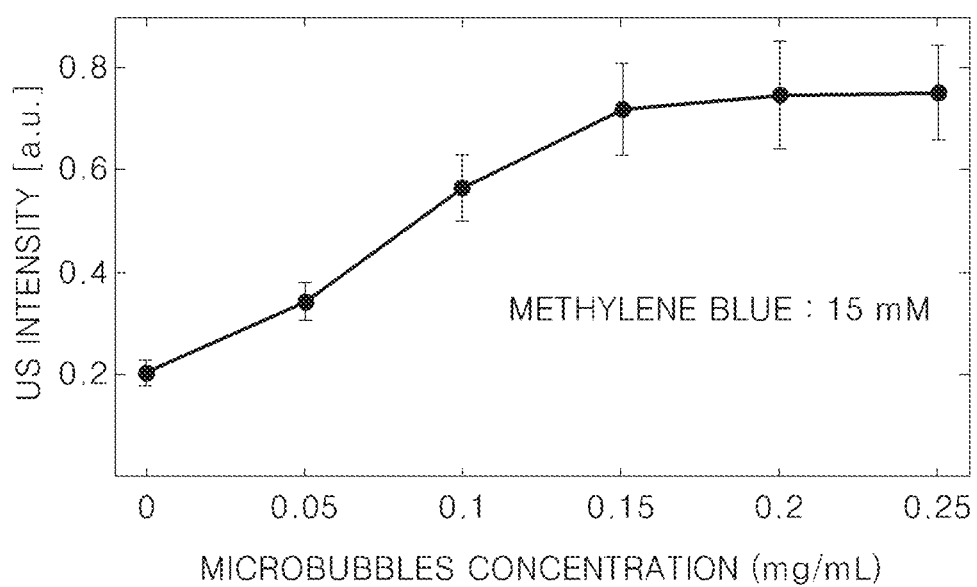
Figure 2E:
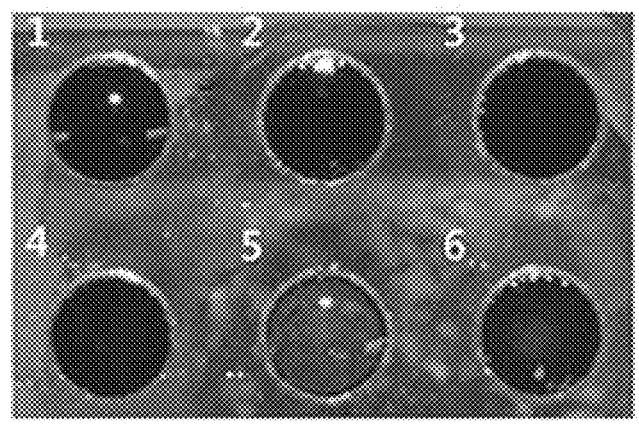
Figure 3A:
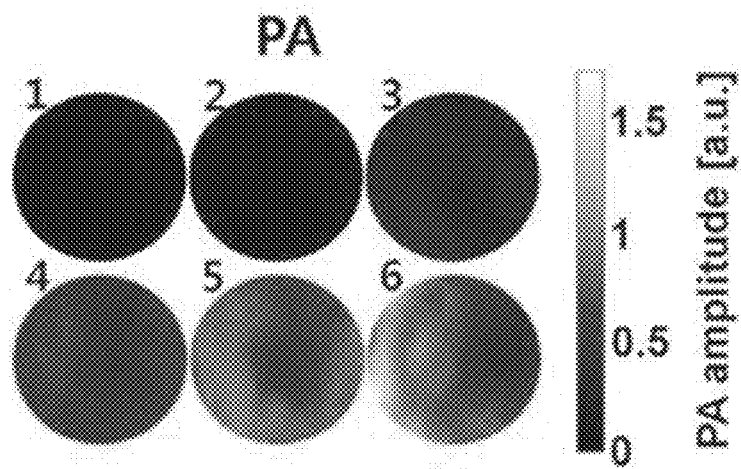
Figure 3B:
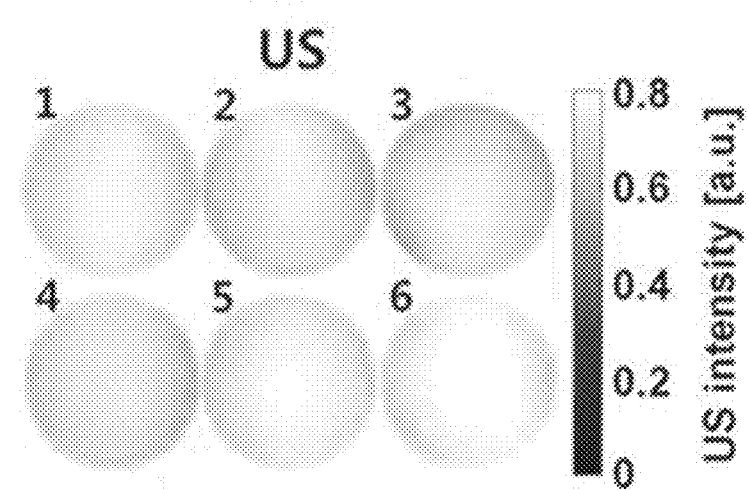
Figure 3C:
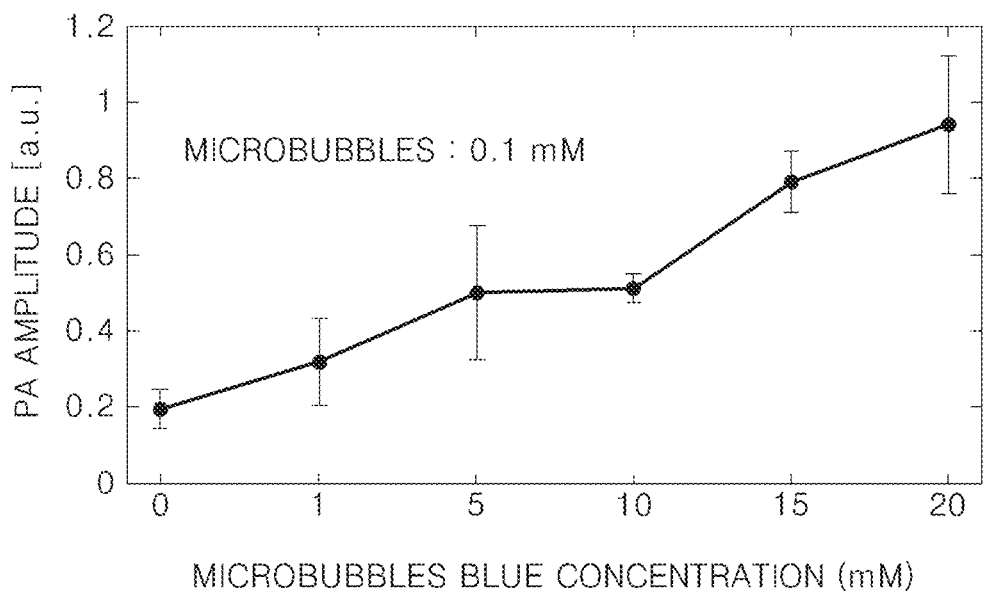
Figure 3D:
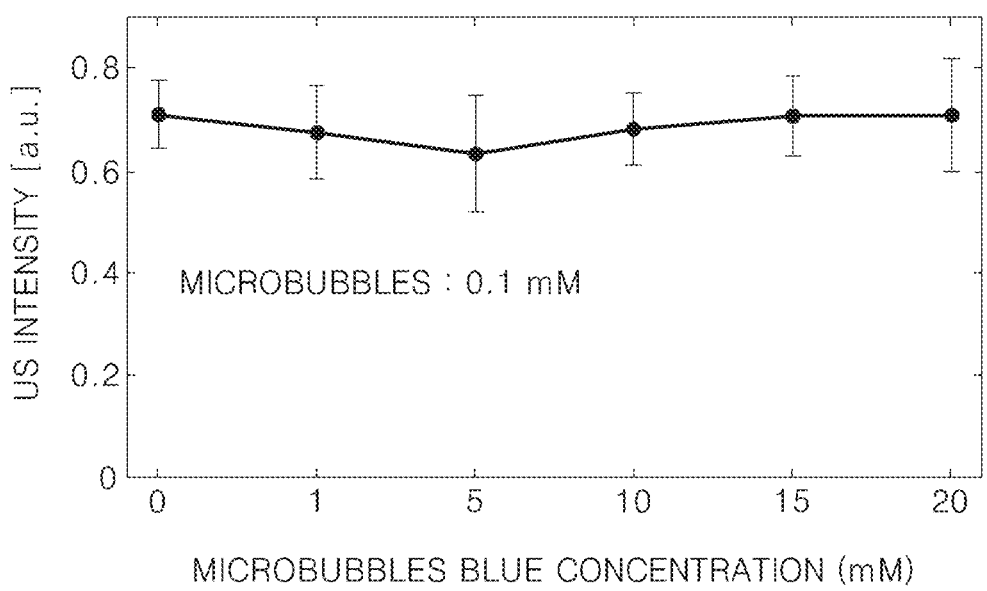
Figure 3E:
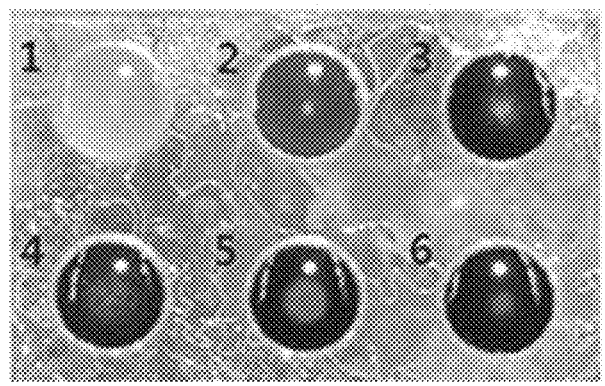
Figure 4A:
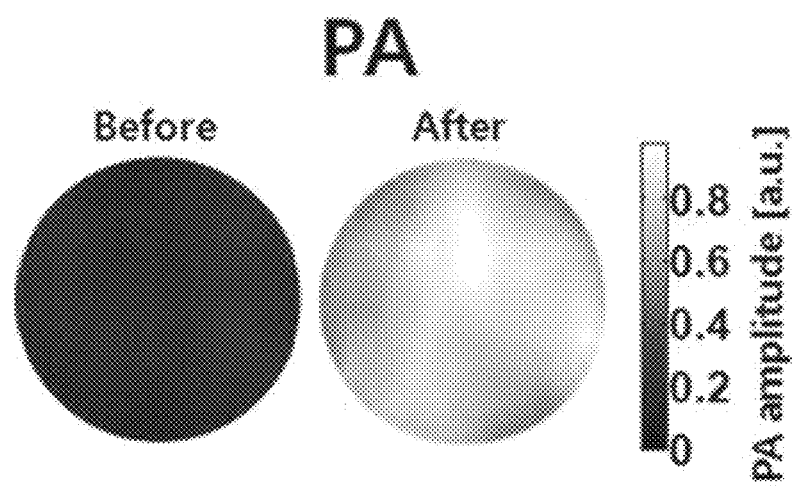
FIGS. 4A-4D shows (4A) photoacoustic imaging of a methylene blue-colored microbubble aqueous solution before and after sonication, (4B) an ultrasound imaging of a methylene blue-colored microbubble aqueous solution before and after sonication, (4C) photographs of samples, and (4D) quantified photoacoustic and ultrasound signals before and after sonication.
Figure 4B:
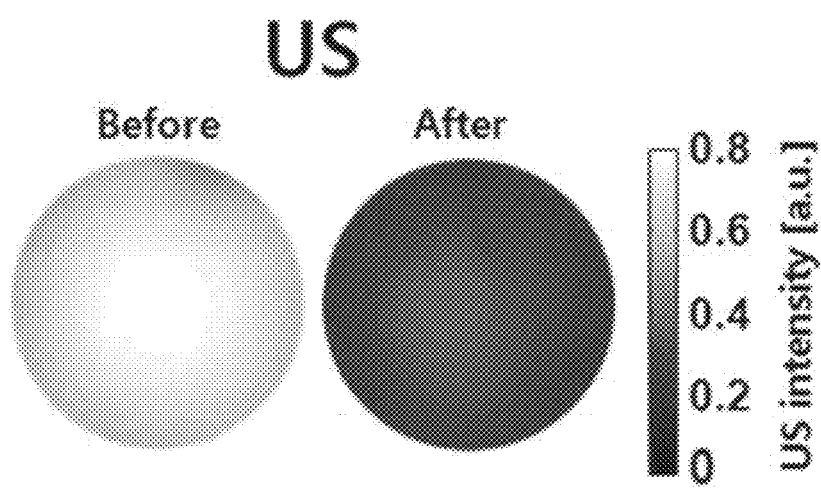
Figure 4C:
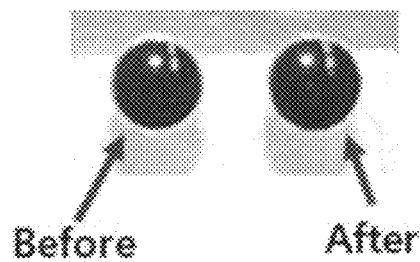
Figure 4D:
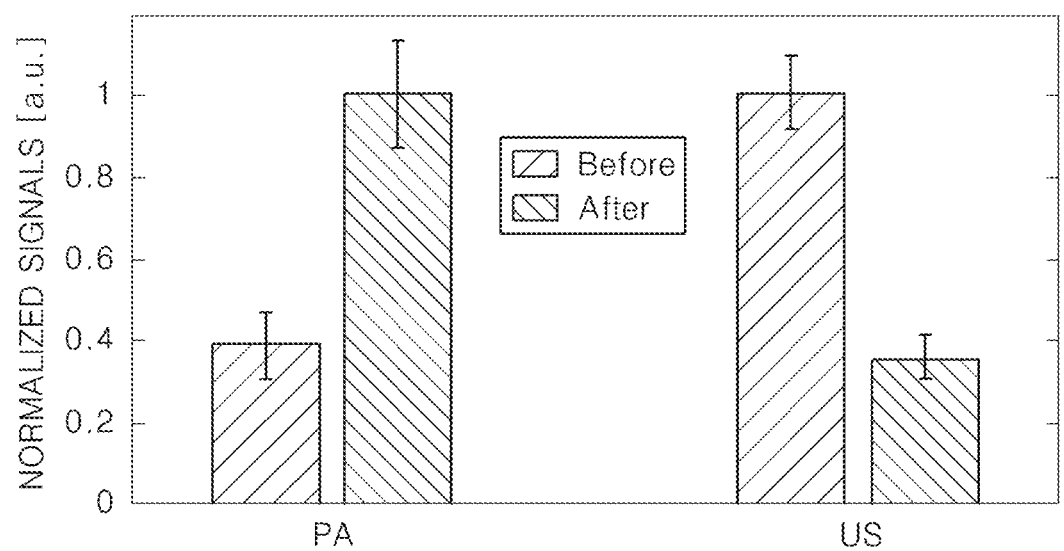
Figure 5D:
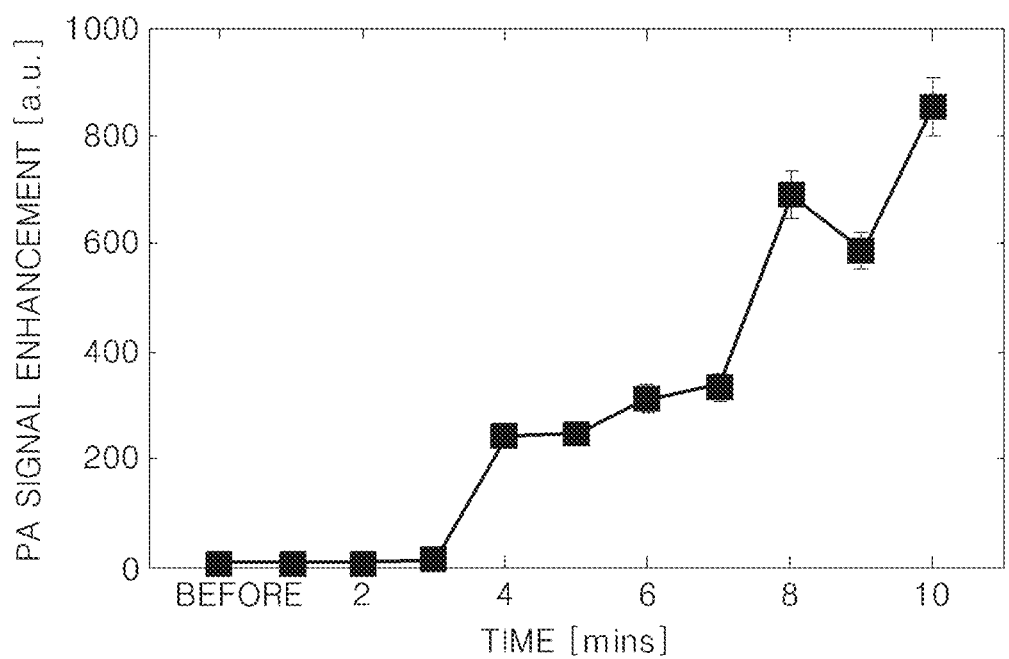

As shown in FIG. 1A, synthesis of methylene blue-dyed microbubble was straightforward and included hydrating a lipid film with a solution of methylene blue, forming an octafluoropropane layer in the vial, and mechanically agitating the vial to form microbubbles. Photographs of methylene blue-dyed microbubble and conventional standard microbubble (hydrated without methylene blue) before and after activation by mechanical agitation are shown in FIG. 1B. Even when a highly concentrated methylene blue solution (15 mM) was used, microbubble formation efficiency negligibly changed compared to control microbubble, and after activation of a 1 mg/mL lipid solution, approximately 4.5×10$^9$ bubbles were formed (FIG. 10). The size of methylene blue-dyed microbubbles was monodispersed with a peak size of just over 3 μm, which was also nearly identical to control microbubbles formed in the absence of methylene blue (FIG. 1D). Due to the similar size distribution of methylene blue-dyed microbubbles to commercial microbubbles, the ultrasound attenuation was dominant at the low frequencies (that is, below 6 MHz), which well matches with previous attenuation measurements using other lipid-capsulated contrast agent [see 19]. The near infrared absorption generated by methylene blue-dyed microbubbles was intense. Even a 1 in 500 dilution of the methylene blue-dyed microbubble solution yielded absorption greater than 1 with spectral properties characteristics of methylene blue and thus unaffected by the microbubbles (see FIG. 1F). To investigate the dual modal imaging capability of methylene blue-dyed microbubbles, photoacoustical and ultrasonical imaging was performed on aqueous solutions of methylene blue-dyed microbubbles by varying the concentration of either microbubbles or methylene blue using a single-element US transducer. As shown in FIG. 2F, the concentration of microbubbles was varied from 0 to 0.25 mg/mL by 0.05 mg/mL whereas the concentration of methylene blue was fixed at 15 mM. The photograph of the six samples is shown in FIG. 2E. FIGS. 2A and 2B show the photoacoustic and ultrasound images of six samples. The quantified photoacoustic and ultrasound signals at various microbubbles concentrations were plotted in FIGS. 2C and 2D, respectively. Interestingly, the photoacoustic signals were decreased when the microbubbles concentration increased. With more than 0.15 mg/mL lipid microbubble concentration, photoacoustic signals were almost identical to the background photoacoustic signals. In contrast, the ultrasound signals increased as the lipid microbubble concentration increased, and reached a plateau after 0.15 mg/mL lipid when the ultrasound signal became saturated. Typically, the amplitude of initial photoacoustic pressure can be expressed as $p_0 = \Gamma \eta_{th} A_e$, where $\Gamma$ is the Grueneisen parameter (dimensionless); $A_e$ is the specific optical absorption (energy deposition, J/m$^3$); and $\eta_{th}$ is the percentage of $A_e$ that is converted into heat. Since the energy deposition ($A_e$) is equal to the product of the optical absorption coefficient of the target ($\eta_{th}$) and the optical fluence (F), the photoacoustic amplitudes are directly proportional to optical absorption coefficients of the target. In this disclosure, although none of these parameters were modulated, photoacoustic signals had interference attenuation. The present disclosure assumes that the microbubbles scatter and absorb the generated photoacoustic waves in the medium while they propagate. Thus, by modulating the concentration of microbubbles in the medium, photoacoustic signals may be attenuated or restored, which present a novel mechanism to modulate photoacoustic signals. As shown in FIG. 3F, the concentration of methylene blue was varied between 0, 1, 5, 10, 15, and 20 mM with the concentration of microbubbles fixed at 0.1 mg/mL. The photograph of the six samples is shown in FIG. 3E. FIGS. 3A and 3B show the photoacoustic and ultrasound images of six samples. The quantified photoacoustic and ultrasound signals at various methylene blue concentrations are plotted in FIGS. 3C and 3D, respectively. As the concentration of methylene blue increased, the photoacoustic signals increased due to greater optical absorption in the solutions. However, the ultrasound intensities remained constant because of the fixed bubble concentration. In this case, the photoacoustic signals are linearly proportional to the optical absorption coefficient, which is based on the principle of conventional photoacoustic wave generation. To further confirm the present disclosure, the switching of photoacoustic and ultrasound signals using sonication was identified. As shown in FIG. 4C, methylene blue-dyed microbubbles with 0.1 mg/mL lipid microbubbles and 15 mM of methylene blue was prepared. The photoacoustic and ultrasound signals of the methylene blue-dyed microbubbles solution were compared before and after sonication. FIGS. 4A and 4B show the photoacoustic and ultrasound images of the sample before and after sonication, respectively. The quantified signals are plotted in FIG. 4D. It is clear that the photoacoustic signal was initially attenuated by microbubbles. However, it recovered after the bubbles were destroyed by sonication. The photoacoustic amplitude increased 2.5 times. Conversely, the ultrasound signals were initially strong, but decreased 2.5 times following sonication. Moreover, to prove this restoration and explore the practicability of this mechanism, methylene blue-dyed microbubbles were disrupted and the photoacoustic signals were recovered using a clinically modified photoacoustic imaging scanner. As shown in FIG. 5A, obtained was a control photoacoustic image of two vials (e.g., left filled with methylene blue-dyed microbubbles and right filled with water) before the methylene blue-dyed microbubbles were disturbed. Two white dotted circles represent the locations of the vials in the medium. The photoacoustic probe detected the signals from the top in the image which was indicated by a yellow dotted arrow (see FIG. 5A). The front surface of the left vial (i.e., filled with methylene blue-dyed microbubbles) was clearly visible while the right vial (i.e. filled with water) was photoacoustically invisible. 50 V of ultrasound pulse (based on intensity) was applied for 3 minutes. However, photoacoustic signals were not capable of being recovered (see FIG. 5B), and the restoration was significantly enhanced after 10 minutes (see FIG. 5C) FIG. 5D shows the photoacoustic signal enhancement vs. high voltage ultrasound application time. The photoacoustic signal was improved by almost 817 times at 10 minutes post-application. Compared with the restoration enhancement obtained using our bench-top system, the improvement using the clinical system was extremely dramatic. According to the present disclosure, the unwanted bulky bubbles in the vial floated up to the top surface over the time period. Thus, when the photoacoustic signals from the side were measured, measurements were not interfered with the floated bulky bubbles. However, when the signals were measured from the top (i.e., bench-top experiments), the photoacoustic wave propagation was significantly disturbed. Thus, the enhancement acquired using our bench-top system was only 2.5 times. To prove this, experimental geometry was changed in the clinical system. The vials were positioned horizontally, and the ultrasound probe scanned them from the top. Then, the photoacoustic signal enhancement was only limited to 25 times or less.

CONCLUSION

These results show that methylene blue microbubbles as a dual modality contrast agent are effectively used for ultrasound and activatable photoacoustic imaging. According to the present disclosure, the photoacoustic signals were significantly suppressed according to the increase of the microbubble concentration in the methylene blue-dyed microbubbles solution (with fixed methylene blue concentration). Also, even when the concentration of methylene blue increases (a concentration of microbubble is fixed), ultrasound intensity does not change. In addition, high powered ultrasound generated by a clinical ultrasound imaging scanner burst the microbubbles and drastically (817 times) recovered photoacoustic signals. This is a truly innovative mechanism to modulate photoacoustic signal generation. Conventionally, one or more parameters with respect to the initial photoacoustic amplitude (for example, Grueneisen coefficient, heat conversion efficiency, optical absorption coefficient, or optical induction) within an object are required to be adjusted to control the photoacoustic signals. However, by using microbubbles dyed with dye according to the present disclosure, these parameters are not needed to be considered any more. From a clinical point of view, both methylene blue and microbubbles have been widely used in clinical practices. From an imaging system perspective, both custom-made bench-top and clinically feasible imaging scanners have been utilized in this study. Thus, the clinical translationabilities of methylene blue-dyed microbubbles and the clinical photoacoustic imaging system are significantly high.

According to the present disclosure, a microbubble used as a contrast agent for ultrasound imaging may burst due to high voltage of ultrasound, and the burst microbubble may effectively act as a contrast agent for photoacoustic imaging. Based on this point, the present disclosure discloses a new apparatus and method for combined photoacoustic and ultrasound diagnosis.

REFERENCE DOCUMENTS 1. (a) Beard, P., Biomedical photoacoustic imaging. Interface focus 2011, 1 (4), 602-31; (b) Kim, C.; Favazza, C.; Wang, L. V., In vivo photoacoustic tomography of chemicals: high-resolution functional and molecular optical imaging at new depths. Chemical reviews 2010, 110 (5), 2756-82; (c) Wang, L. V.; Hu, S., Photoacoustic tomography: in vivo imaging from organelles to organs. Science 2012, 335 (6075), 1458-62.
2. (a) Laufer, J.; Johnson, P.; Zhang, E.; Treeby, B.; Cox, B.; Pedley, B.; Beard, P., In vivo preclinical photoacoustic imaging of tumor vasculature development and therapy. Journal of biomedical optics 2012, 17 (5), 056016; (b) Yao, J.; Maslov, K. I.; Wang, L. V., In vivo photoacoustic tomography of total blood flow and potential imaging of cancer angiogenesis and hypermetabolism. Technology in cancer research & treatment 2012, 11 (4), 301-7.
3. Yao, J.; Xia, J.; Maslov, K. I.; Nasiriavanaki, M.; Tsytsarev, V.; Demchenko, A. V.; Wang, L. V., Noninvasive photoacoustic computed tomography of mouse brain metabolism in vivo. NeuroImage 2013, 64, 257-66.
4. (a) Laufer, J.; Norris, F.; Cleary, J.; Zhang, E.; Treeby, B.; Cox, B.; Johnson, P.; Scambler, P.; Lythgoe, M.; Beard, P., In vivo photoacoustic imaging of mouse embryos. Journal of biomedical optics 2012, 17 (6), 061220; (b) Zemp, R. J.; Song, L.; Bitton, R.; Shung, K. K.; Wang, L. V., Realtime photoacoustic microscopy of murine cardiovascular dynamics. Optics express 2008, 16 (22), 18551-6.
5. Jiao, S.; Jiang, M.; Hu, J.; Fawzi, A.; Zhou, Q.; Shung, K. K.; Puliafito, C. A.; Zhang, H. F., Photoacoustic ophthalmoscopy for in vivo retinal imaging. Optics express 2010, 18 (4), 3967-72.
6. (a) Kim, C.; Erpelding, T. N.; Jankovic, L.; Wang, L. V., Performance benchmarks of an array-based hand-held photoacoustic probe adapted from a clinical ultrasound system for non-invasive sentinel lymph node imaging. Philosophical transactions. Series A, Mathematical, physical, and engineering sciences 2011, 369 (1955), 4644-50; (b) Ermilov, S. A.; Khamapirad, T.; Conjusteau, A.; Leonard, M. H.; Lacewell, R.; Mehta, K.; Miller, T.;

Oraevsky, A. A., Laser optoacoustic imaging system for detection of breast cancer. Journal of biomedical optics 2009, 14 (2), 024007.
7. (a) Kim, C.; Song, K. H.; Gao, F.; Wang, L. V., Sentinel lymph nodes and lymphatic vessels: noninvasive dual-modality in vivo mapping by using indocyanine green in rats—volumetric spectroscopic photoacoustic imaging and planar fluorescence imaging. Radiology 2010, 255 (2), 442-50; (b) Wang, B.; Zhao, Q.; Barkey, N. M.; Morse, D. L.; Jiang, H., Photoacoustic tomography and fluorescence molecular tomography: a comparative study based on indocyanine green. Medical physics 2012, 39 (5), 2512-7; (c) Morgounova, E.; Shao, Q.; Hackel, B. J.; Thomas, D. D.; Ashkenazi, S., Photoacoustic lifetime contrast between methylene blue monomers and self-quenched dimers as a model for dual-labeled activatable probes. Journal of biomedical optics 2013, 18 (5), 56004.
8. (a) Cai, X.; Li, W.; Kim, C. H.; Yuan, Y.; Wang, L. V.; Xia, Y., In vivo quantitative evaluation of the transport kinetics of gold nanocages in a lymphatic system by noninvasive photoacoustic tomography. ACS nano 2011, 5 (12), 9658-67; (b) Kim, C.; Song, H. M.; Cai, X.; Yao, J.; Wei, A.; Wang, L. V., In vivo photoacoustic mapping of lymphatic systems with plasmon-resonant nanostars. Journal of materials chemistry 2011, 21 (9), 2841-2844; (c) Jokerst, J. V.; Cole, A. J.; Van de Sompel, D.; Gambhir, S. S., Gold nanorods for ovarian cancer detection with photoacoustic imaging and resection guidance via Raman imaging in living mice. ACS nano 2012, 6 (11), 10366-77; (d) Qin, H.; Zhou, T.; Yang, S.; Chen, Q.; Xing, D., Gadolinium (III)-gold nanorods for MRI and photoacoustic imaging dual-modality detection of macrophages in atherosclerotic inflammation. Nanomedicine 2013.
9. (a) Lovell, J. F.; Jin, C. S.; Huynh, E.; Jin, H.; Kim, C.; Rubinstein, J. L.; Chan, W. C.; Cao, W.; Wang, L. V.; Zheng, G., Porphysome nanovesicles generated by porphyrin bilayers for use as multimodal biophotonic contrast agents. Nature materials 2011, 10 (4), 324-32; (b) Zha, Z.; Deng, Z.; Li, Y.; Li, C.; Wang, J.; Wang, S.; Qu, E.; Dai, Z., Biocompatible polypyrrole nanoparticles as a novel organic photoacoustic contrast agent for deep tissue imaging. Nanoscale 2013, 5 (10), 4462-7.
10. (a) Kim, C.; Erpelding, T. N.; Jankovic, L.; Pashley, M. D.; Wang, L. V., Deeply penetrating in vivo photoacoustic imaging using a clinical ultrasound array system. Biomedical optics express 2010, 1 (1), 278-284; (b) Kim, C.; Erpelding, T. N.; Maslov, K.; Jankovic, L.; Akers, W. J.; Song, L.; Achilefu, S.; Margenthaler, J. A.; Pashley, M. D.; Wang, L. V., Handheld array-based photoacoustic probe for guiding needle biopsy of sentinel lymph nodes. Journal of biomedical optics 2010, 15 (4), 046010.
11. Wilson, S. R.; Burns, P. N., Microbubble-enhanced US in body imaging: what role Radiology 2010, 257 (1), 24-39.
12. (a) Lanza, G. M.; Wickline, S. A., Targeted ultrasonic contrast agents for molecular imaging and therapy. Current problems in cardiology 2003, 28 (12), 625-53; (b) Song, J.; Qi, M.; Kaul, S.; Price, R. J., Stimulation of arteriogenesis in skeletal muscle by microbubble destruction with ultrasound. Circulation 2002, 106 (12), 1550-5.
13. Kim, C.; Qin, R.; Xu, J. S.; Wang, L. V.; Xu, R., Multifunctional microbubbles and nanobubbles for photoacoustic and ultrasound imaging. Journal of biomedical optics 2010, 15 (1), 010510.
14. Wang, Y. H.; Liao, A. H.; Chen, J. H.; Wang, C. R.; Li, P. C., Photoacoustic/ultrasound dual-modality contrast agent and its application to thermotherapy. Journal of biomedical optics 2012, 17 (4), 045001.
15. Wilson, K.; Homan, K.; Emelianov, S., Biomedical photoacoustics beyond thermal expansion using triggered nanodroplet vaporization for contrast-enhanced imaging. Nature communications 2012, 3, 618.
16. Huynh, E.; Lovell, J. F.; Helfield, B. L.; Jeon, M.; Kim, C.; Goertz, D. E.; Wilson, B. C.; Zheng, G., Porphyrin shell microbubbles with intrinsic ultrasound and photoacoustic properties. Journal of the American Chemical Society 2012, 134 (40), 16464-7.
17. Goertz, D. E.; de Jong, N.; van der Steen, A. F., Attenuation and size distribution measurements of Definity and manipulated Definity populations. Ultrasound in medicine & biology 2007, 33 (9), 1376-88.
18. Kim, C.; Jeon, M.; Wang, L. V., Nonionizing photoacoustic cystography in vivo. Optics letters 2011, 36 (18), 3599-601.
19. (a) Gorce, J. M.; Arditi, M.; Schneider, M., Influence of bubble size distribution on the echogenicity of ultrasound contrast agents: a study of SonoVue. Investigative radiology 2000, 35 (11), 661-71; (b) Sarkar, K.; Shi, W. T.; Chatterjee, D.; Forsberg, F., Characterization of ultrasound contrast microbubbles using in vitro experiments and viscous and viscoelastic interface models for encapsulation. The Journal of the Acoustical Society of America 2005, 118 (1), 539-50.

What is claimed is:

1. A combined photoacoustic and ultrasound diagnosis method, comprising operations of:
   (a) transmitting a first ultrasound signal to a subject to which a contrast agent having microbubbles has been administered, detecting an echo signal generated due to reflection of the first ultrasound signal by the microbubbles, and displaying an ultrasound image produced based on the echo signal, wherein the first ultrasound signal has a mechanical index at which the microbubbles do not burst;
   (b) transmitting a second ultrasound signal to the subject to burst the microbubbles to form microbubble flakes, wherein the second ultrasound signal has a mechanical index at which the microbubbles burst; and
   (c) irradiating the subject with a laser signal, detecting a photoacoustic signal generated due to the microbubble flakes stimulated by the laser signal, and then, displaying a photoacoustic image produced based on the photoacoustic signal,
   wherein the microbubbles each comprise:
   a lipid shell colored with dye; and
   a filling gas encapsulated by the lipid shell,
   wherein a concentration of the dye in a dye solution used to hydrate the lipid shell is in a range of 0.5 mM to 20 mM, and
   wherein the dye is azure blue, evans blue, indocyanine green, brilliant blue, nile blue, methylene blue, or a combination thereof.

2. The combined photoacoustic and ultrasound diagnosis method of claim 1, wherein the first ultrasound signal has the mechanical index of less than 0.5.

3. The combined photoacoustic and ultrasound diagnosis method of claim 1, wherein the microbubbles contain a drug that is to be delivered to an organ in the subject.

4. The combined photoacoustic and ultrasound diagnosis method of claim 1, wherein the second ultrasound signal has the mechanical index of 0.5 to 1.9.

5. The combined photoacoustic and ultrasound diagnosis method of claim 1, wherein the microbubbles contain a drug that is to be delivered to an organ in the subject, and the operation (b) begins when arriving of the microbubbles at the organ is confirmed.

6. The combined photoacoustic and ultrasound diagnosis method of claim 1, wherein the dye absorbs incident light having a wavelength of 500 nm to 1,300 nm.

7. The combined photoacoustic and ultrasound diagnosis method of claim 1, wherein the concentration of the dye in the dye solution used to hydrate the lipid shell is in a range of 15 mM to 20 mM.

8. The combined photoacoustic and ultrasound diagnosis method of claim 1, wherein the lipid shell comprises a phospholipid.

9. The combined photoacoustic and ultrasound diagnosis method of claim 8, wherein the phospholipid comprises 1,2-dipalmitoyl-sn-glycero-3-phosphatidic acid (DPPA); 1,2-dipalmitoyl-sn-glycero-3-phosphatidylcholine (DPPC); 1,2-distearoyl-sn-glycero-3-phosphocholine (DSPC); 1,2-dimyristoyl-sn-glycero-3-phosphocholine (DMPC); 1,2-dibehenoyl-sn-glycero-3-phosphocholine (DBPC); 1,2-diarachidoyl-sn-glycero-3-phosphatidylcholine (DAPC); 1,2-dilignoceroyl-sn-glycero-3-phosphatidylcholine (DLgPC); 1,2-dipalmitoyl-sn-glycero-3-[phosphor-rac-(1-glycerol)] (DPPG); or a mixture thereof.

10. The combined photoacoustic and ultrasound diagnosis method of claim 1, wherein a particle diameter of the lipid shell is in a range of 0.5 µm to 10 µm.

11. The combined photoacoustic and ultrasound diagnosis method of claim 1, wherein a wall thickness of the lipid shell is in a range of 1 nm to 200 nm.

12. The combined photoacoustic and ultrasound diagnosis method of claim 1, wherein the filling gas is a biologically inactive gas.

13. The combined photoacoustic and ultrasound diagnosis method of claim 1, wherein the filling gas comprises perfluorocarbon, sulphur hexafluoride, perfluoromethane, perfluoroethane, perfluoropropane, perfluorobutane, perfluoropentane, perfluorohexane, perfluoroheptane, perfluorooctane, perfluorononane, perfluorodecane, perfluorobenzene, perfluorotriethylamine, perfluorooctylbromide, or a mixture thereof.

14. The combined photoacoustic and ultrasound diagnosis method of claim 1, wherein a drug is located inside the lipid shell.

15. The combined photoacoustic and ultrasound diagnosis method of claim 1, wherein the operation (c) begins when or after the operation (b) begins.

16. A combined photoacoustic and ultrasound diagnosis apparatus, comprising
a laser irradiation unit which irradiates a subject with a laser signal;
an ultrasound signal transducer which transmits a first ultrasound signal to the subject, detects an echo signal generated due to reflection of the first ultrasound signal by microbubbles in the subject, transmits a second ultrasound signal to the subject to burst the microbubbles to form microbubble flakes, and detects a photoacoustic signal generated due to stimulation of the microbubble flakes by the laser signal, wherein the first ultrasound signal has a mechanical index at which the microbubbles do not burst, and the second ultrasound signal has a mechanical index at which the microbubbles burst;
an image processor which produces a photoacoustic image based on the photoacoustic signal and an ultrasound image based on the echo signal; and
a display unit which displays the photoacoustic image and ultrasound image,
wherein the microbubbles each comprise:
a lipid shell colored with dye; and
a filling gas encapsulated by the lipid shell,
wherein the dye is azure blue, evans blue, indocyanine green, brilliant blue, nile blue, methylene blue, or a combination thereof,
wherein the ultrasound signal transducer detects the photoacoustic signal when bursting the microbubbles, and
wherein a concentration of the dye in a dye solution used to hydrate the lipid shell is in a range of 0.5 mM to 20 mM.

17. A combined photoacoustic and ultrasound diagnosis method, comprising operations of:
(a) transmitting a first ultrasound signal to a subject to which a contrast agent having microbubbles has been administered, detecting an echo signal generated due to reflection of the first ultrasound signal by the microbubbles, and displaying an ultrasound image produced based on the echo signal, wherein the first ultrasound signal has a mechanical index at which the microbubbles do not burst;
(b) transmitting a second ultrasound signal to the subject to burst the microbubbles to form microbubble flakes, wherein the second ultrasound signal has a mechanical index at which the microbubbles burst; and
(c) irradiating the subject with a laser signal, detecting a photoacoustic signal generated due to the microbubble flakes stimulated by the laser signal, and then, displaying a photoacoustic image produced based on the photoacoustic signal,
wherein the microbubbles each comprise:
a lipid shell colored with dye; and
a filling gas encapsulated by the lipid shell, wherein the dye is azure blue, evans blue, indocyanine green, brilliant blue, nile blue, methylene blue, or a combination thereof,
wherein the operation (c) begins after the operation (b) begins, and
wherein a concentration of the dye in a dye solution used to hydrate the lipid shell is in a range of 0.5 mM to 20 mM.

18. A combined photoacoustic and ultrasound diagnosis apparatus, comprising a laser irradiation unit which irradiates a subject with a laser signal;
an ultrasound signal transducer which transmits a first ultrasound signal to the subject, detects an echo signal generated due to reflection of the first ultrasound signal by microbubbles in the subject, transmits a second ultrasound signal to the subject to burst the microbubbles to form microbubble flakes, and detects a photoacoustic signal generated due to stimulation of the microbubble flakes by the laser signal, wherein the first ultrasound signal has a mechanical index at which the microbubbles do not burst, and the second ultrasound signal has a mechanical index at which the microbubbles burst;
an image processor which produces a photoacoustic image based on the photoacoustic signal and an ultrasound image based on the echo signal; and
a display unit which displays the photoacoustic image and ultrasound image,
wherein the microbubbles each comprise:
a lipid shell colored with dye; and
a filling gas encapsulated by the lipid shell, wherein the dye is azure blue, evans blue, indocyanine green, brilliant blue, nile blue, methylene blue, or a combination thereof,
wherein the ultrasound signal transducer detects the photoacoustic signal after bursting the microbubbles, and
wherein a concentration of the dye in a dye solution used to hydrate the lipid shell is in a range of 0.5 mM to 20 mM.

* * * * *